(12) United States Patent
Temtsin-Krayz et al.

(10) Patent No.: US 11,844,859 B2
(45) Date of Patent: *Dec. 19, 2023

(54) DRY POWDER COMPOSITIONS FOR INTRANASAL DELIVERY

(71) Applicant: Nasus Pharma Ltd., Tel Aviv (IL)

(72) Inventors: Galia Temtsin-Krayz, Ashdod (IL); Dalia Megiddo, M.P. Judean Hills (IL); Tair Lapidot, Lapid (IL); Carolina Abrutzky, Lapid (IL)

(73) Assignee: Nasus Pharma Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/952,278

(22) Filed: Nov. 19, 2020

(65) Prior Publication Data
US 2021/0128462 A1 May 6, 2021

Related U.S. Application Data

(63) Continuation-in-part of application No. 16/636,178, filed as application No. PCT/IL2018/050914 on Aug. 19, 2018, now Pat. No. 11,331,270.

(60) Provisional application No. 62/547,858, filed on Aug. 20, 2017.

(51) Int. Cl.
| | | |
|---|---|---|
| *A61K 9/00* | (2006.01) | |
| *A61K 31/485* | (2006.01) | |
| *A61K 47/26* | (2006.01) | |
| *A61K 47/38* | (2006.01) | |

(52) U.S. Cl.
CPC .......... *A61K 9/0075* (2013.01); *A61K 31/485* (2013.01); *A61K 47/26* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 6,462,090 B1 | 10/2002 | Slutsky et al. | |
| 6,866,039 B1 | 3/2005 | Wright et al. | |
| 6,945,953 B2 | 9/2005 | Wright | |
| 8,673,360 B2 | 3/2014 | Nagata et al. | |
| 8,875,704 B2 | 11/2014 | Djupesland et al. | |
| 9,211,253 B2 | 12/2015 | Crystal et al. | |
| 9,556,260 B2 | 1/2017 | Frey, II et al. | |
| 11,116,723 B2 * | 9/2021 | Temtsin-Krayz | A61K 47/26 |
| 2001/0049391 A1 | 12/2001 | Alfonso et al. | |
| 2003/0178440 A1 | 9/2003 | Wright | |
| 2005/0028813 A1 | 2/2005 | Harrison | |
| 2007/0119451 A1 | 5/2007 | Wang et al. | |
| 2007/0178166 A1* | 8/2007 | Bernstein | A61K 9/0075 |
| | | | 424/502 |
| 2008/0292713 A1 | 11/2008 | Seville et al. | |
| 2009/0041800 A1 | 2/2009 | Woiwode et al. | |
| 2009/0246281 A1 | 10/2009 | Goller et al. | |
| 2011/0033544 A1 | 2/2011 | Nagata et al. | |
| 2012/0145150 A1 | 6/2012 | Donovan et al. | |
| 2014/0073562 A1 | 3/2014 | Djupesland | |
| 2015/0010633 A1 | 1/2015 | Li et al. | |
| 2016/0220489 A1 | 8/2016 | Fleming et al. | |
| 2016/0354288 A1 | 12/2016 | Uehara et al. | |

FOREIGN PATENT DOCUMENTS

| | | | |
|---|---|---|---|
| EP | 0588255 A1 | 3/1994 | |
| EP | 2648788 A1 | 10/2013 | |
| JP | 2004-523594 A | 8/2004 | |
| WO | 02/080884 A2 | 10/2002 | |
| WO | 2009/050726 | 4/2009 | |
| WO | 2016133863 A1 | 8/2016 | |
| WO | 2017180659 A1 | 10/2017 | |
| WO | WO-2017180659 A1 * | 10/2017 | ........... C07D 211/58 |

OTHER PUBLICATIONS

Narcan Nasal Spray efficacy for emergency treatment of opioid overdone, Ontario HIV Treatment Network, available online Sep. 5, 2019). (Year: 2019).*
Naloxone intranasal (Rx) Information Sheet, Medscape, available online Nov. 22, 2015.
Singh, Alok Pratap, et al., "SLN approach for nose-to-brain delivery of alprazolam", Drug Delivery and Translational Research, 2012, vol. 2, Issue 6, pp. 498-507.
Kosfeld, Michael, et al., "OxyContin increases trust in humans", Nature, vol. 435, Jun. 2, 2005, pp. 673-676.
Benedict, Christian, et al., "Intranasal Insulin to Improve Memory Function in Humans", Neuroendocrinology, 2007, vol. 86, pp. 136-142.
Freiherr, Jessica, et al., "Intranasal Insulin as a Treatment for Alzheimer's Disease: A Review of Basic Research and Clincial Evidence", CNS Drugs 2013, vol. 27, pp. 505-514.
Reger, M., et al., "Effect of intranasal insulin on cognition in memory impaired older adults: Modulation by APOE genotype", Neurobiology of Aging, 2006, vol. 27, pp. 451-458.
Jin, Kunlin, et al., "Cerebral Neurogensis is Induced by Intranasal Administration of Growth Factors", Neurol. 2003, vol. 53, pp. 405-409.
Sherr, Jennifer, et al., "Glucagon Nasal Powder: A Promising Alternative to Intramuscular Glucagon in Youth with Type 1 Diabetes", Diabetes Care 2016, vol. 39, pp. 555-562.
Grassin-Delyle, Stanislas, et al., "Intranasal drug delivery: An efficient and non-invasive route for systemic administration: focus on opioids", Pharmacology & Therapeutics, 2012, vol. 134, pp. 366-379.
Operation Manual (Original), Mini Spray Dryer B-290 BUCHI Labortechnik AG, May 31, 2016, 82 pages.
Aundhia, C.J., et al., "Spray Drying in the Pharmaceutical Industry—A Review", Indo American Journal of Pharm Research. 2011:2(1), Jun. 15, 2011, pp. 125-138.

(Continued)

*Primary Examiner* — Melissa S Mercier
(74) *Attorney, Agent, or Firm* — Banner & Witcoff, Ltd.

(57) ABSTRACT

Dry powder pharmaceutical compositions for intranasal administration include an opioid receptor antagonist, e.g. naloxone, as active ingredient, and dosage unit forms thereof. Methods of treating opioid overdose include administering the dry powder compositions.

23 Claims, 20 Drawing Sheets

(56) References Cited

OTHER PUBLICATIONS

Goyal, Sandhya, et al., "Brain Targeting Through Nasal Route: An Overview on Transport Mechanism, Delivery Systems and Evaluation", 2013, World Journal of Pharmacy and Pharmaceutical Sciences, vol. 2, Issue 4, pp. 1607-1640.
EMA Guideline: Guideline on the Pharmaceutical Quality of Inhalation and Nasal Products, Jun. 2006, 27 pages.
Nasal Spray and Inhalation Solution, Suspension, and Spray Drug Products—Chemistry, Manufacturing, and Controls Documentation, Jul. 2002, 49 pages.
Obaidi, Mohammad, et al., "Improved Pharamacokinetics of Sumatriptan With Breath Powered Nasal Delivery of Sumatriptan Powder", Headache, 2013, vol. 53, pp. 1323-1333.
Fuseau, Eliane, et al.,, "Clinical Pharmacokinetics of Intranasal Sumatriptan", Clin Pharmacokinet., 2002, vol. 41(11), pp. 801-811.
FDA Guidance for Industry (Chemistry, Manufacturing & Controls Documentation): Metered-Dose Inhaler (MDI) & Dry Powder Inhaler (DPI) Drug Products—Quality Considerations (Oct. 1998), 50 pages.
Krieter, Phillip, et al., "Pharamacokinetics Properties and Human Use Characteristics of an FDA-Approved Intranasal Naloxone Product for the Treatment of Opioid Overdose", The Journal of Clinical Pharmacology, May 5, 2016.
"B-290 Mini Spray Dryer Operation Manual", BUCHI Labortechnik AG, May 31, 2016.
Boström Emma et al, "In Vivo Blood-Brain Barrier Transport of Oxycodone in the Rat: Indications for Active Influx and Implications for Pharmacokinetics/Pharmacodynamics", Metabolism and Disposition, vol. 34, No. 9, (2006), 8 pages.
Clarke, S. F. J., Dargan, P. I., Jones, A. L., "Naxalone in opioid poisoning: walking the tightrope", Emerg Med J 2005, vol. 22(9), pp. 612-616.
World Health Organization, "Community of management of opioid overdose, WHO guidelines Approved byt eh Guidelines Review Committee. World Health Organization, Geneva.", 2014, downloaded from http://apps.who.int/iris/bitstream/10665/137462/1/9789241548816_engpdf?ua=1&ua=1, 88 pages.
Buajordet, Ingebjorg, Naess, Anne-Cathrine, Jacobsen, Dag, Brors, Odd, "Adverse events after naloxone treatment of episodes of suspected acute opioid overdose", European Journal of Emergency Medicine, 2004, Volune 11, No. 1, pp. 19-23.
Rudde, Rose A., Aleshire, Noah, Zibbell, Jon, Gladden, Matthew, "Increases in Drug and Opioid Overdose Deaths—United States, 2004-2014", Center for Disease Control and Prevention Morbidity and Mortality Weekly Report, Jan. 1, 2016, vol. 64(5-51), pp. 1378-1382.
NARCAN (naloxone hydrochloride) Nasal Spray Prescribing Information. Adapt Phara, Inc., USA, Nov. 2015, 18 pages.
Nyxoid-EPAR Product Information. Mundipharama Corporation (Ireland) Ltd, Nov. 2017, 29 pages.
Food and Drug Administration (FDA), News Release Nov. 18, 2015, FDA moves quickly to approve easy-to-use nasal spray to treat opioid overdose, 4 pages.
Lewis, Christa R., Vo, Hoa T., Fishman, Marc, "Intransal naloxone and related strategies for opioid overdose intervention by nonmedical personnel: a review", Substance Abuse and Rehabilitation, 2017:8, pp. 79-95.
Clement, John G., and Copeman, H. Taffy, "Soman and Sarin Induce a Long-Lasting Naloxone-Reversible Analgesia in Mice", Life Sciences, 1984, vol. 34, pp. 1415-1422.
United Nations Office on Drugs and Crime (UNODC).World Drug Report 2016, United Nationals publication, Sales No. E.16.XI.7. downloaded from https://www.unodc.org/wdr2016, 1 page.

\* cited by examiner

DRY POWDER COMPOSITIONS FOR INTRANASAL DELIVERY

CROSS-REFERENCE TO RELATED APPLICATIONS

The present application is a continuation-in-part of U.S. patent application Ser. No. 16/636,178 filed on Aug. 19, 2018 (ex PCT Application PCT/IL2018/050914), claiming priority from U.S. Application Ser. No. 62/547,858 filed on Aug. 20, 2017, all fully incorporated herein by reference.

TECHNICAL FIELD

The present application relates to delivery of drugs in powder form by intranasal administration of a pharmaceutical composition comprising at least one active agent, particularly an opioid receptor antagonist, and lactose or a lactose functional analogue as dry powder particles of specific particle size. The present application further relates to methods for the preparation of the said pharmaceutical compositions and, more particularly, to methods of treatment of a subject in need thereof by administration of at least one pharmaceutical active agent via intranasal delivery to the uppermost region of the nasal cavity.

BACKGROUND

Several publications are referred to herein, indicated by Arab numerals in parenthesis. A full list of these reference appears at the end of the description immediately preceding the claims. These publications as well as all other publications mentioned herein are fully incorporated herein by reference.

Intranasal delivery has a number of compelling advantages over other routes of administration, namely its non-invasiveness, rapid attainment of therapeutically relevant concentrations to the bloodstream, no first-pass metabolism, and ease of administration. Viable nasal delivery technologies have the potential to enable drug developers in creating innovative medicines using already approved products by delivering them through new routes of administration.

The intranasal delivery of drugs utilizes devices of several types, such as nebulizers, pressurized devices, dry powder sprayers, and bi-directional nasal devices. Dry powders are used in intranasal drug delivery due to many advantages of using this dosage form including the improved stability, administration of larger doses and lack of microbial growth (no need for preservatives). The administration of intranasal powders may improve patient compliance, especially if the smell and taste of the delivered composition comprising excipients is unpleasant. Compared to drug solutions, the administration of powders covering of the upper and back parts of the nasal cavity and being a prolonged contact with the nasal mucosa can result in improved delivery of the drug. Powder form is suitable for delivery of both small molecules and biologics, especially peptides, hormones and antibodies.

Traditionally, intranasal preparations have been used for local administration of anti-histamines, decongestants and steroids, for alleviation of cold, allergy symptoms and/or nasal congestion. More recently, researchers' attention has been focused on two specific areas:

(1) The potential rapid drug absorption into the systemic circulation provided by turbinate and lymphoid tissues located at the back of the nasal cavity. This has already been in use in a number of indications e.g. migraine and pain relief, osteoporosis, vaccines, etc., and (2) The potential of the "Nose to Brain" (N2B) delivery to the central nervous system (CNS) presented by the olfactory region at the top of the nasal cavity, for the treatment of central nervous system (CNS) diseases. Blood brain barrier (BBB) prevents the treatment of neurological diseases by many potential drugs. Among them are Alzheimer's, Parkinson's, stroke, spinal cord injury, depression, and other CNS disorders. The blood-brain barrier is related primarily to the endothelium of the brain capillaries, through which few molecules can pass.

There are many advantages to the intranasal administration of medications that include, among others, a direct route to the blood stream, avoidance of hepatic first pass metabolism, higher bioavailability, ease and convenience of non-invasive manipulation, and proximity to the central nervous system. In addition, direct delivery of drugs to the brain provides the possibility of a better therapeutic-toxic ratio than with systemic drug delivery.

The olfactory region inside the nasal cavity, involved in sensing odors and chemicals, provides a unique and direct connection between the brain and the external environment. A number of studies reported drugs that do not or poorly cross the blood-brain barrier, but are rapidly delivered to the CNS when delivered intranasally, preferably delivered directly to the turbinate and lymphoid tissues located at the back of the nasal cavity. A free communication exists between the nasal submucosal interstitial space and the olfactory perineuronal space, which is contiguous with a subarachnoid extension that surroundings the olfactory nerve. The olfactory epithelium is capable of metabolizing some drugs. The olfactory neuronal pathway includes both the intracellular (intraneuronal) and extracellular (extraneuronal) pathway into the brain. After reaching the olfactory bulb and/or trigeminal region the active ingredient/s may penetrate other brain regions by diffusion, which may also be facilitated by arterial pulsation. In addition, intranasally administered drugs may also partially enter into CNS after its penetration into the systemic blood circulation.

Mostly hydrophilic drugs like dopamine and picolinic acid can be transported through the olfactory pathway. In case of lipophilic drugs, the systemic route is better than olfactory route because it can cross the blood brain barrier (BBB). Singh et al showed that alprazolam loaded in solid-lipid nanoparticles was rapidly transferred to the rabbit brain via intranasal route, bypassing the blood-brain barrier (1). The enhanced rate and extent of transport may help in reducing the dose and dosing frequency, thereby providing a better compliance for ambulatory patients. Another study confirmed that intranasal oxytocin administration could increase confidence in human subjects (2).

Moreover, an increasing number of studies on both animals and human subjects suggested that intranasal drug delivery could be used to transfer not only small molecules but also large sized biologics into the CNS by bypassing the BBB. Benedict et al showed that insulin administration by the intranasal route may improve memory and mood of healthy adults (3). Freiherr et al (4) and Reger et al (5) demonstrated that the memory of AD patients may also be approved without altering blood levels of insulin or glucose. Jin et al reported that intranasal administration of either fibroblast growth factor-2 or heparin-binding epidermal growth factor may have potential as neurogenesis-promoting therapeutic agents (6). All aforementioned pharmaceutical active ingredients were administered to the nasal cavity as sprays.

While intranasal delivery specifically to the olfactory region potentially provides a route for delivery of agents to the CNS, the olfactory region is difficult to access using conventional nasal delivery devices. The olfactory region is located in the uppermost region of the nasal cavity, where less than 10% of the inhaled air flows. Conventional nasal sprays deposit the majority of the drug in the lower region of the nasal cavity, with very little drug reaching the olfactory region. Improved devices for the spray delivery to the olfactory region are described in US Patent Application No. 20070119451. The devices include a nosepiece and an elongated tubular member slidably disposed within the nosepiece for movement between a retracted position and an extended position. The tubular member is in flow communication with a reservoir containing the substance to be delivered. During the use, the tubular member extends from the device, to direct the substance toward the olfactory region. However, this reference does not disclose delivery of solid dry powders. Similar devices are disclosed in US 20030178440, U.S. Pat. Nos. 6,866,039, 6,945,953 and US 20050028813.

U.S. Pat. No. 9,556,260 described methods and compositions for the treatment of CNS disorders via intranasal administration of pooled human immunoglobulin G. As shown therein, intranasal administration allows the directed delivery of intact IgG to the brain bypassing the need to pass through the BBB. This results in greater efficiency for the treatment and reduces the necessary IgG dose that must be administered to achieve the desired effect. Whilst pooled human IgG is isolated from donated human plasma, pooled IgG is a limited resource. Therefore, if made possible, the reduction in the effective dose of IgG would effectively increase the therapeutic potential. Furthermore, intranasal administration of IgG nearly eliminates the systemic exposure caused by intravenous administration, improving the overall safety profile of the treatment. Also, it would be beneficial to intranasally administer IgG to the brain in the absence of permeability enhancers, some of which has neuro-stimulation effects themselves.

US Patent Application No. 20140073562 relates to a nasal delivery device and method of delivering a substance, preferably comprising oxytocin, non-peptide agonists thereof and antagonists thereof, preferably as one of a liquid, as a suspension or solution, or a powder to the nasal airway of a subject, preferably the posterior region of the nasal airway, and preferably the upper posterior region of the nasal airway which includes the olfactory bulb and the trigeminal nerve, and preferably in the treatment of neurological conditions and disorders.

U.S. Pat. No. 8,875,704 described a delivery device and method of delivering a powdered substance, in particular a triptan, such as sumatriptan, to the posterior region of a nasal cavity of a subject, in particular for the treatment of headaches, for example, cluster headaches and migraine, and neuropathic pain. WO 2016133863 provides a nasal powder formulation containing glucagon or a glucagon analog for nasal administration, useful in the treatment of hypoglycemia, and in particular the treatment of severe hypoglycemia. Sherr et al (7) demonstrated in their clinical trials that glucagon nasal powder delivering glucagon transmucosally might be a promising alternative to intramuscular glucagon in adults and youth with type 1 diabetes, however, the authors did not mention that glucagon can be delivered from nose to brain.

U.S. Pat. No. 6,462,090, US 20080292713, US 20150010633, US 20160354288 and other similar publications described dry powder inhalers (DPI) of therapeutic agents for pulmonary delivery. US 20150010633 disclosed the preparation of aerosol formulations of ondansetron useful exclusively for pulmonary delivery, because the active drug ondansetron, when administered by inhalation, must penetrate deep into the lungs in order to show physiological action. However, none of the publications above teach or mention the delivery of therapeutic agents to the brain via intranasal administration. Accordingly, there is an unmet need for methods of treating central nervous system (CNS) disorders with known and new active agents that provide specific targeting to the CNS (in terms of direct administration primarily to the brain), reduce systemic distribution of the active agents and lower the therapeutically effected doses needed for administration.

Opioid overdoses are a worldwide epidemic, affecting both drug abusers and patients treated with prescribed medications. Overdose deaths from heroin and other opioids represent a significant international public health concern, accounting for approximately 106,000 deaths annually (12) and this figure is increasing, particularly in the USA (13).

Opioids intoxication is manifested by reduced consciousness and respiratory depression which may deteriorate to cardiac arrest and death. The antidote naloxone is the drug of choice for treatment of opioid overdose. Naloxone is a semisynthetic congener of the opioid analgesic oxymorphone. While the mechanism of action of naloxone is not fully understood, the preponderance of evidence suggests that naloxone hydrochloride is a pure opioid antagonist. It does not possess any "agonistic" or opioid-type properties.

Naloxone is usually administered intravenously (IV) or intramuscularly (IM) with a starting dose of 0.4-2.0 mg and titrated to desired response. Reversal of symptoms is rapid, but acute withdrawal symptoms can be precipitated, particularly in opioid-dependent subjects following IV administration and higher doses (14). Overall, however, the drug has an excellent safety profile and, when administered in the absence of opioids, exhibits little pharmacologic activity (15).

Most of the overdose incidents occur outside the hospitals and require intervention by unaffected bystanders. Many stakeholders have advocated provision of naloxone to people who are not medically trained that are likely to witness such episodes, thus allowing immediate assistance in this life-threatening situation (16). This, in fact, has led the World Health Organization (WHO) to issue in 2014 guidelines recommending that 'people likely to witness an opioid overdose should have access to naloxone' (17).

This principle was adopted for a nasal liquid spray (Narcan® Nasal Spray, Adapt Pharma, PA, USA) having a concentration of 40 mg/mL delivered in 0.1 mL doses. The bioavailability of the nasal formulation relative to IM was 0.47 (18). The FDA approved this nasal naloxone product in 201 (19). Another product, Nyxoid 1.8 mg Nasal Spray (Mundipharma Corporation, Ireland) has been authorized for marketing in the European Union in 2017 (20).

U.S. Pat. No. 9,775,838 (Adapt Pharma & Opiant Pharmaceuticals) describes a method of treating opioid overdose, essentially by delivering 25-200 µL spray of a pharmaceutical solution comprising naloxone, an isotonicity agent and benzalkonium chloride from a pre-primed device adapted for nasal delivery into a nostril of a patient, delivering between about 4 mg and about 10 mg naloxone. It is described that the patient experiences a geometric mean naloxone $C_{max}$ not less than about 3 ng/mL following a single spray administration.

U.S. Pat. No. 10,441,538 (Hikma Pharmaceuticals) describes a liquid spray formulation for sublingual and nasal administration comprising about 9% w/w naloxone and various excipients, without an isotonicity agent or a buffer. Administration of naloxone in formulations with co-solvents resulted in superior bioavailability. Further, the addition of permeation enhancers such as caprylic acid and benzalkonium chloride resulted in further increase in bioavailability.

As mentioned above, dry powders have many advantages in intranasal drug delivery, including improved stability, administration of larger doses and lack of microbial growth (no need for preservatives).

As shown in the Examples below intranasal of naloxone exhibited significant advantages.

SUMMARY

Disclosed herein is a pharmaceutical composition in a form of dry powder for intranasal administration, comprising at least one opioid receptor antagonist as active ingredient, said composition comprising a first type of solid particles comprising said at least one opioid receptor antagonist and a second type of solid particles comprising pharmaceutically acceptable disaggregating agent, wherein at least 90% of said first type particles are of a mean particle size of about 10 to about 30 microns, and less than about 10% of said first type particles are of a mean particle size equal to or below about 10 microns and said second type particles are of a mean particle size greater than that of the first type particles.

In the presently disclosed pharmaceutical composition, less than about 5% of said first type particles can be of a mean particle size of or below 5 microns, said second type particles are of a mean size of about 50 to about 200 microns, for example a mean size of about 50 to about 150 microns.

In the presently disclosed pharmaceutical composition, said first type particles are of a substantially spherical form and said second type particle are of an irregular shape.

The presently disclosed pharmaceutical composition comprises said dis-aggregating agent as the only excipient for preventing aggregation of the dry powder particles of the active agent and preserving their original size and shape in said composition.

In the presently disclosed pharmaceutical composition, said at least one opioid receptor antagonist can be any one of naloxone, naltrexone, almivopan, methylnaltrexone, naloxegon or naldemidine and pharmaceutically acceptable salts thereof and solvates or hydrates thereof, wherein said salt is any of chloride, bromide, oxalate, chloride, or tosylate.

In the presently disclosed pharmaceutical composition, said disaggregating agent can be any one of lactose monohydrate, lactose, a lactose functional analogue, or any mixture of at least two thereof. In specific embodiments, said disaggregating can be any one of dextrose, sorbitol, mannitol, maltitol and xylitol, a cellulose or cellulose derivative, or starch or starch derivative, or any mixture of at least two thereof.

In the presently disclosed pharmaceutical composition, the weight ratio between said first type particles and said second type particle can be between about 1:9 to about 9:1. The weight ratio between said first type particles and said second type particle can between about 1:9 to about 9:1. In specific embodiments, the weight ratio between said first type particles and said second type particle is from about 1:9 to about 4:6, specifically about 2:8.

In a second aspect, disclosed is a naloxone pharmaceutical composition in the form of dry powder for intranasal administration, comprising as active agent naloxone or a pharmaceutically acceptable salt thereof, said composition comprising a first type of solid particles comprising said naloxone or pharmaceutically acceptable salt thereof, and a second type of solid particles comprising lactose monohydrate as disaggregation agent, wherein at least about 90% of said first type particles are of a mean particle size of about 10-30 microns and less than about 10% of said first type particles are of a mean particle size equal to or below about 10 microns and said second type particles are of a mean particle size greater than that of the first type particles, providing a metered therapeutically effective nominal dose of said naloxone or pharmaceutically acceptable salt thereof.

In the presently disclosed pharmaceutical composition of said second aspect, the weight ratio between said first type particles and said second type particle is from about 1:9 to about 4:6, specifically about 2:8.

The pharmaceutical composition of said second aspect, comprises about 20% w/w, about 15% w/w, about 10% w/w, about 8% w/w or about 5% w/w naloxone or said pharmaceutically acceptable salt thereof or solvate or hydrate thereof.

Also disclosed is a disposable dose unit form for single intranasal administration to a subject of a pharmaceutical composition according to any one of claims 1 to 11, wherein said dose unit is loaded with a predetermined dose of the composition and provides the subject with a therapeutically effective metered dose of said pharmaceutically active opioid receptor antagonist.

The said disposable dose unit form can be loaded with a predetermined dose of the composition and provides the subject with a therapeutically effective metered dose naloxone or said pharmaceutically acceptable salt thereof.

In some embodiments of the dose unit, the therapeutically effective metered dose naloxone or pharmaceutically acceptable salt thereof is 4 mg per single administration.

Also disclosed is a for intranasal administration of naloxone comprising at least one said dose unit for single intranasal administration comprising a naloxone pharmaceutical composition as disclosed herein and instructions for use.

Further disclosed is a method of treating opioid overdose/intoxication and/or a symptom thereof in a patient in need thereof, said method comprising intranasally administering to said patient a therapeutically effective amount of a composition described herein or a single dose of a composition as contained in the dose unit describe herein.

The said symptom associated with opioid overdose/intoxication is any one of respiratory depression, central nervous system depression, cardiovascular depression, altered level consciousness, miotic pupils, hypoxemia, acute lung injury, aspiration pneumonia, sedation, hypotension, unresponsiveness to stimulus, unconsciousness, stopped breathing; erratic or stopped pulse, choking or gurgling sounds, blue or purple fingernails or lips, slack or limp muscle tone, contracted pupils, and vomiting. At times, said patient is not breathing.

The single intranasal administration in the disclosed method can provide the patient with a dose of 1.5, 2, 3 or 4 mg naloxone or pharmaceutically acceptable salt thereof.

In the disclosed method of treatment, administration of the at least one dose unit can be repeated at 2 to 3 minute intervals, up to a cumulative dose of from about 8 mg to about 10 mg and up to about 15 mg of naloxone.

In some embodiments, the present method of treatment further comprises administration of an opioid, that can be administered simultaneously with the naloxone or separately.

In the disclosed method of treatment, by the naloxone unit dose intranasal administration the major part of over 50% of the first type naloxone particles reach turbinates region in the intranasal cavity, and less than 1% of said first type particles reach the lungs of said patient.

In specific embodiments, by the naloxone unit dose intranasal administration at least 85% of the first type naloxone particles reach turbinates region in the intranasal cavity, less than about 10% of said first type naloxone particle reach other region of the intranasal cavity, and less than 1% of said first type particles reach the lungs of said patient.

The pharmaceutical composition of the present disclosure is prepared by a modified spray drying method, for example as shown in FIG. 2 and as described in U.S. patent application Ser. No. 16/636,178, fully incorporated herein by reference.

Clear superiority of the intranasal composition of the present invention to the brain and plasma is shown in the Examples below.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

Disclosed embodiments will be understood and appreciated more fully from the following detailed description taken in conjunction with the appended figures.

DETAILED DESCRIPTION

Figure 1:
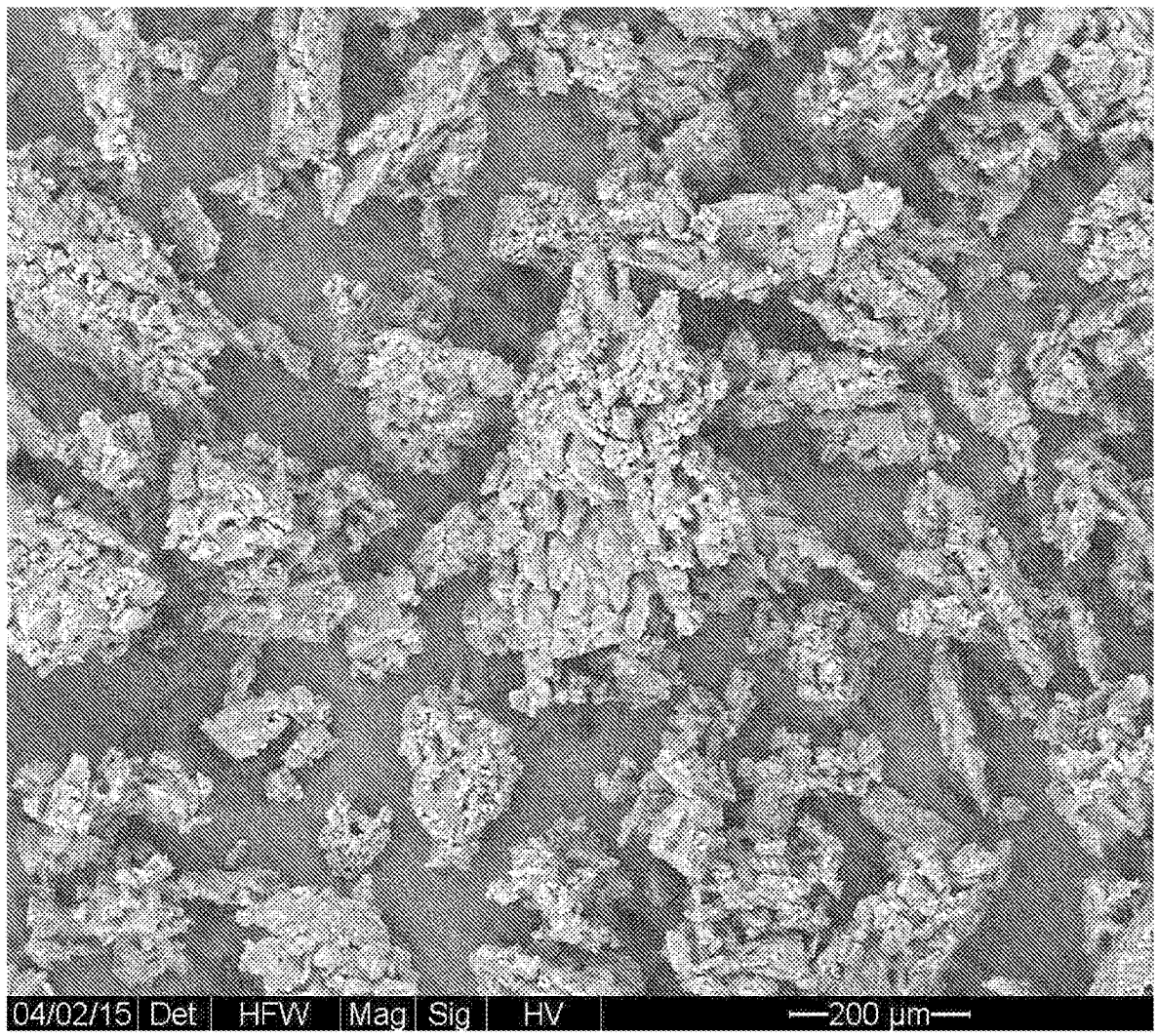
FIG. 1 shows the Scanning Electron Microscopy (SEM) image of sumatriptan succinate agglomerated powder, when the receiving chamber is empty (not prefilled with a diluent or disaggregation agent).

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The terminology used herein is for describing particular embodiments only and is not intended to be limiting of the invention. The term "comprising" and "comprises", used in the claims, should not be interpreted as being restricted to the components and steps listed thereafter; they do not exclude other components or steps. They need to be interpreted as specifying the presence of the stated features, integers, steps and/or components as referred to, but does not preclude the presence and/or addition of one or more other features, integers, steps or components, or groups thereof. Thus, the scope of the expression "a composition comprising A and B" should not be limited to compositions consisting only of components A and B. Also, the scope of the expression "a method comprising the steps X and Z" should not be limited to methods consisting exclusively of those steps.

Unless specifically stated, as used herein, the term "about" is understood as within a range of normal tolerance in the art, for example within two standard deviations of the mean. In one embodiment, the term "about" means within 10% of the reported numerical value of the number with which it is being used, preferably within 5% of the reported numerical value. For example, the term "about" can be immediately understood as within 10%, 9%, 8%, 7%, 6%, 5%, 4%, 3%, 2%, 1%, 0.5%, 0.1%, 0.05%, or 0.01% of the stated value. In other embodiments, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges, for example from 1-3, from 2-4, and from 3-5, as well as 1, 2, 3, 4, 5, or 6, individually. This same principle applies to ranges reciting only one numerical value as a minimum or a maximum. Unless otherwise clear from context, all numerical values provided herein are modified by the term "about". Other similar terms, such as "substantially", "generally", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value.

As used herein, the term "and/or" includes any combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The terms "active agent", "pharmaceutical active agent", "active", "API", "active pharmaceutical ingredient", "active substance", "active molecule", "active compound" or "drug" are used interchangeably.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealised or overly formal sense unless expressly so defined herein. Well-known functions or constructions may not be described in detail for brevity and/or clarity.

In one aspect, disclosed herein is a pharmaceutical composition for intranasal administration in the form of dry powder, comprising at least one opioid receptor antagonist as active ingredient, the composition comprising a first type of solid particles comprising the at least one opioid receptor antagonist and a second type of solid particles comprising pharmaceutically acceptable dis-aggregating agent, wherein at least 90% of said first type particles are of a mean particle size of about 10 to about 30 microns, and less than about 10% of said first type particles are of a mean particle size equal to or below about 10 microns and said second type particles are of a mean particle size greater than that of the first type particles. In specific embodiments of this aspect of the present disclosure less than 5% of said first type particles are of a mean particle size of less than 5 microns. The first type particles are of substantially spherical form. The second type particles are of irregular form and of a size of about 50 to about 200 microns.

In embodiments of this aspect of the present disclosure, the opioid receptor antagonist is any one of naloxone, naltrexone, almivopan, methylnaltrexone, naloxegon or naldemidine, but not limited thereto, and pharmaceutically acceptable salts thereof, and hydrates and solvates of these salts. Exemplary salts are bromides for example, methylnaltrexone bromide, oxalates, for example naloxegon oxalate, chlorides for example naloxone HCl, tosylates, for example naldemidine tosylate, and others are possible. Within the context of this disclosure "naloxone" is to be taken to mean also pharmaceutically acceptable salts of naloxone, for example but not limited those slats mentioned above, with naloxone hydrochloride, in anhydrous or solvated or hydrated form thereof as a specific example.

In specific embodiments of this aspect of the present disclosure, the opioid receptor antagonist is naloxone hydrochloride.

The terms opioid receptor "antagonist" and "inverse agonist" may be used herein interchangeably.

The terms "opioid" or "opiate" as used herein is to be taken to mean at least one of natural or synthetic or semi-synthetic narcotics, including codeine, fentanyl, heroin, hydromorphone, meperidine, methadone, morphine and derivatives, oxymorphone, oxycodone HCl, hydrocodone bitartrate, hydromorphone, opium and drugs such as tramadol and tapentadol, as well as others.

The disaggregating agent comprised in the disclosed composition is an inert carrier, as described in detail below. It is to be noted that "disaggregating agent", "carrier", "diluent" and "deagglomerating agent" are used herein interchangeably, and refer to an inert ingredient added to the pharmaceutical composition, comprising the said second type particles.

Figure 16:
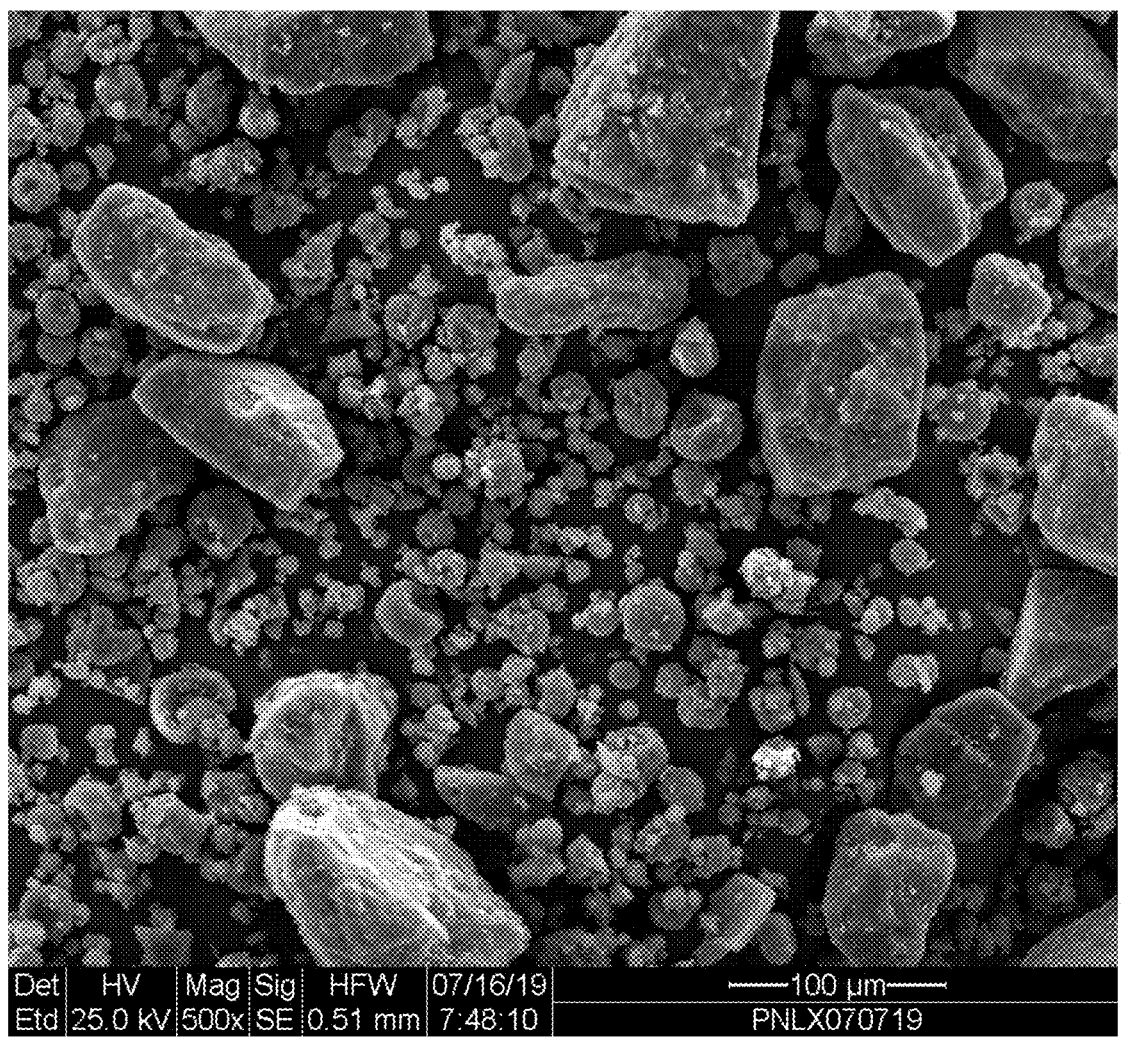
FIG. 16 shows the SEM images of lactose monohydrate (large shapeless particles) and naloxone hydrochloride particles (small spherical particles) of dry powder for intranasal delivery formulation (see Example 27).
Figure 17:
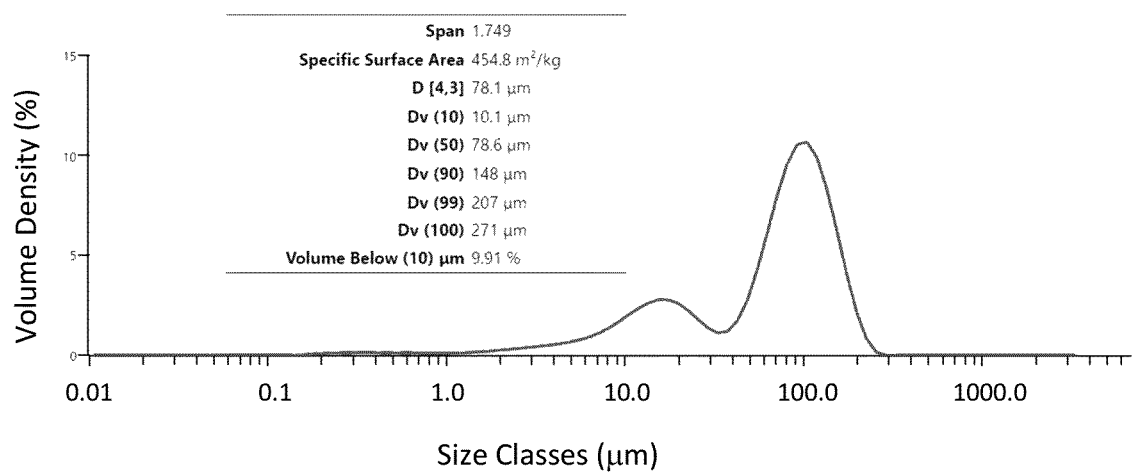
FIG. 17 shows the particle size distribution of the pharmaceutical composition of the embodiments (see Example 28). Two populations of the particles are clearly seen: the Naloxone HCl active agent in the range of 5-30 microns (m) and lactose in the range of 40-240 microns; D(10)=10.1 µm; D(50)=78.6 µm; D(90)=148 µm.

The intranasal compositions comprising an opioid receptor antagonist according to the present disclosure is prepared according to the methods described herein. The preparation of a specific composition is described in the Examples below. Example 26 describes the preparation of naloxone hydrochloride composition with lactose monohydrate as the disaggregating agent. SEM imaging of the composition is shown in FIG. 16. The particle distribution of the composition of Example 26 is described in Example 28 and shown in FIG. 17.

In specific embodiments, the naloxone compositions prepared according to the herein described methods, can be designed for desired naloxone levels, for example a level of at least about 22.2% w/w naloxone hydrochloride or a hydrate thereof in the form of microspheres when said microspheres are separated and dis-agglomerated by at least 77.8% of lactose monohydrate particles. In the composition exemplified in Example 26, the loading of naloxone hydrochloride obtained was about 26% w/w. The obtained compositions can be diluted by mixing with a further amount of the disaggregating agent (lactose monohydrate in Example 26), to give a desired level of naloxone hydrochloride. This additional mixing is included in the general process described herein. Thus, for example, in Example 26 the crude product was mixed with an additional amount of lactose monohydrate, to give a product with final level of 20% w/w naloxone hydrochloride. This final composition was then introduced into a disposable dose device, as described below, to provide a dose of from about 4 to about 12 mg naloxone hydrochloride upon single intranasal administration.

The pharmaceutical composition according to the present disclosure can be contained in disposable dose units for intranasal administration, providing predetermined metered dose of naloxone, specifically naloxone hydrochloride. An example of such dose unit is illustrated in FIG. 2A, which shows Unit Dose Powder Device (UDS), manufactured by Aptar Pharma. Devices of this type for powder spraying are user friendly and designed to enable systemic delivery of small and accurately metered doses of drug formulations by patients or caregivers who are not healthcare professionals or medically trained.

The present disclosure further relates to a dose unit form (also referred to as dose unit device, dose device or drug device), specifically a disposable dose unit form, for intranasal administration to a subject of a single dose of a\the pharmaceutical composition according to the present disclosure, which comprises as active ingredient an opioid receptor antagonist, specifically naloxone or pharmaceutically acceptable salts thereof such as naloxone hydrochloride, wherein the dose unit is loaded with a predetermined dose of the composition and provides the subject with a metered dose the pharmaceutically active ingredient comprised in the composition. The preparation of naloxone hydrochloride dose units is described in Example 29. The dose units prepared each contained a total of 20 mg composition, of which 4 mg were naloxone hydrochloride (200 mg/g). Dose uniformity was tested for 10 dose units, as described in Example 30. As shown in Example 31, the dose unit devices loaded with combination exhibited good product stability under normal and accelerated (at about 40° C. and 75% relative humidity) storage conditions. Importantly, although devoid of preserving agents, the present dose unit forms are storage stable. In addition to the dose unit devices described above and in the Examples and drawing, the naloxone composition of the present disclosure can be administered using syringe-driven device and pump-driven spraying atomizers. Bi-dose and multiple-dose administration devices are also contemplated within the scope of the present invention.

Figure 18:
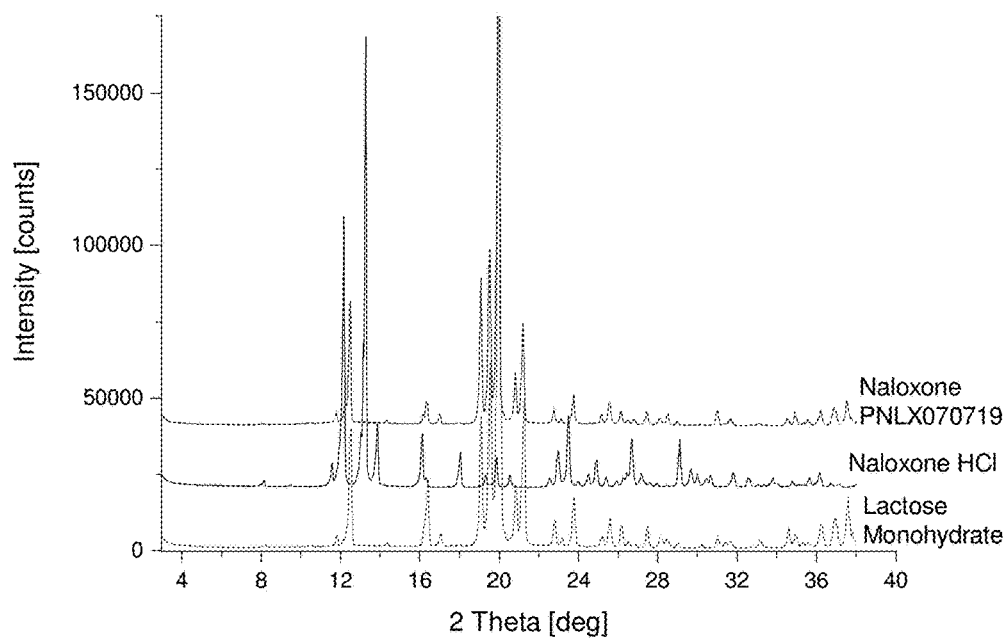
FIG. 18 shows XRD pattern images for Lactose Monohydrate, Naloxone HCl and Naloxone HCl microparticles (see Example 32)
Figure 19:
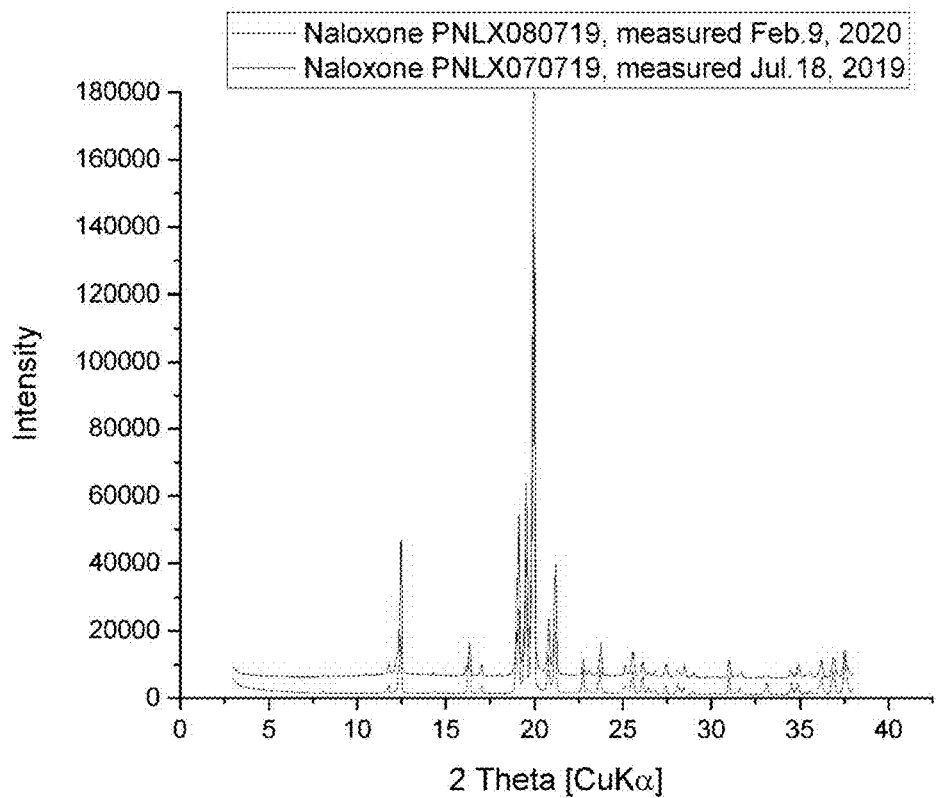
FIG. 19 shows XRD pattern images for Initial Naloxone microsphere powder (lower) and stored for 6 months (upper) (see Example 32)

Surprisingly, the naloxone contained in the dose devices of the present disclosure was retained in amorphous form, as shown in Example 32 and FIGS. 18 and 19.

Compositions according to this aspect of the invention which contain naloxone or pharmaceutically acceptable salt thereof as the active opioid receptor antagonist and dose units thereof are also referred to herein as naloxone compositions, respectively naloxone dose units.

The naloxone compositions of the present disclosure are particularly intended for treatment of opioid overdose and acute opioid overdose, also referred to as opioid intoxication, which is described in detail above. Treatment of opioid overdose as referred to herein is to be taken to mean alleviating or reversing the effects of the opioid overdose, as well as symptoms associated therewith such as depression and even loss of consciousness and respiratory depression, and any condition that is responsive to and can be ameliorated by administration of opioid receptor antagonists, such as various intoxications, for example after exposure to nerve gas (naloxone induced long-lasting analgesia in mice exposed to sarin and soman (21)). The naloxone compositions and dose units thereof according to the present disclosure have been shown to be significantly effective.

Figure 20:
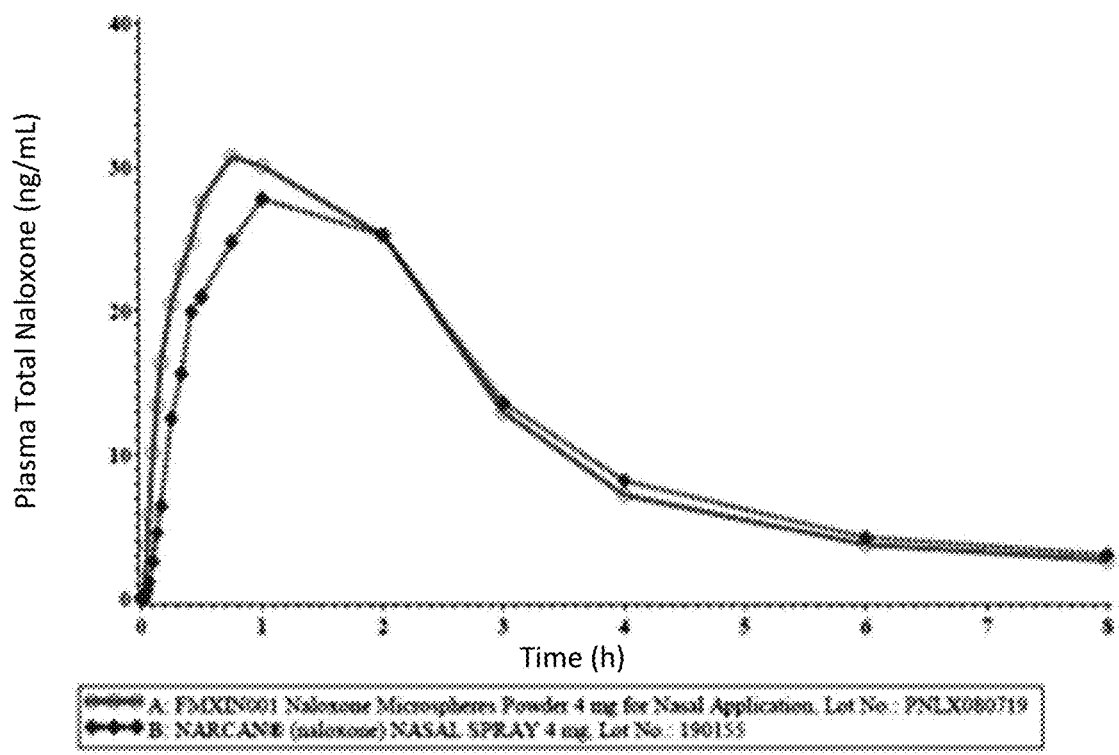
FIG. 20 shows the Mean Plasma Total Naloxone Concentration-Time Profile (Linear Scale)
Figure 21:
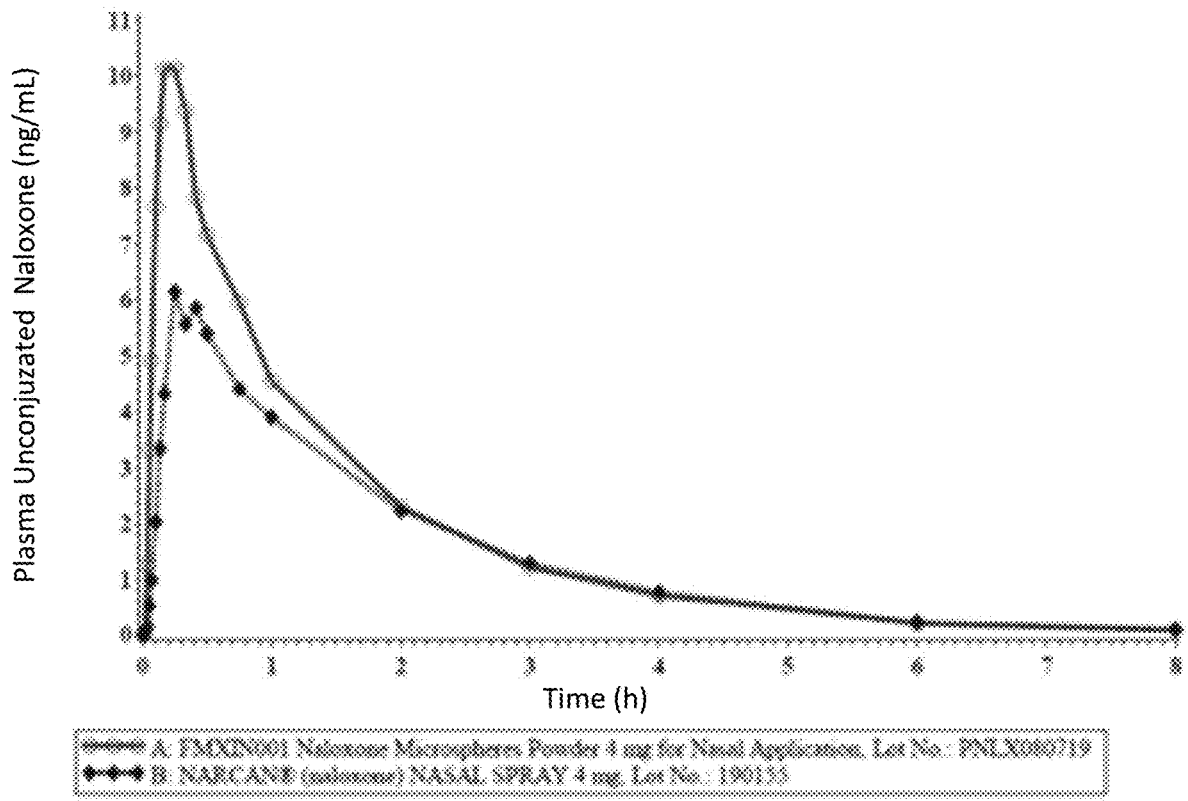
FIG. 21 shows the Mean Plasma Unconjugated Naloxone Concentration-Time Profile (Linear Scale) (Example 33)

Example 33 presents the results of a comparative pharmacokinetic study, which compared the bioavailability and bioequivalence of a naloxone composition according to the present invention (Microspheres Nasal Powder, also referred to herein as FMXIN001) providing 4 mg naloxone per single administration, and the commercially available "NARCAN®", a liquid nasal spray, a Nasal Spray also providing 4 mg naloxone per single administration. FIG. 20 shows the Mean Plasma Total Naloxone Concentration-Time Profile (Linear Scale) and FIG. 21 shows the Mean Plasma Unconjugated Naloxone Concentration-Time Profile (Linear Scale).

Clear superiority of the powder intranasal spray composition of the present invention compared to the NARCAN® liquid intranasal is shown. These results are particularly surprising considering that both compositions were nasally administered in the same dose of 4 mg naloxone hydrochloride.

Notably, the present naloxone composition is devoid of permeation enhancer or other additives that can enhance absorption, as described in the prior art (e.g. U.S. Pat. No. 10,441,538, supra).

A naloxone unit according to the present disclosure can contain from about 1.5 to about 15 mg of the active naloxone or naloxone salt.

As shown in Example 34, when the naloxone intranasal powder formulation in accordance with the present disclosure was administered by means of a unit dose device for intranasal administration as described herein (by Aptar), loaded with the formulation, a high proportion of the naloxone particle of at least 86% reached the nasal turbinates region, more specifically about 35% were the middle part and 51% in the upper olfactory area, while less than 10% of the naloxone particles were in the nose and less than 1% reached the lungs, providing at treated subject with very high effective amounts of naloxone and improved therapeutic effect.

Still further, provided herein is a kit for the treatment/reversal of opioid overdose. The kit comprises at least one dose unit of naloxone powder composition as disclosed herein and instructions for use. The dose unit can be single-dose, bi-dose or multiple-dose unit.

In one embodiment, a pharmaceutical composition in a form of dry powder for intranasal (nose-to-brain) N2B administration to a patient in need thereof comprises solid particles of at least one active agent and solid particles of a diluent, said pharmaceutical composition being substantially free of excipients other than the solid diluent, wherein said pharmaceutical composition having at least 90% of the particles of said at least one active agent with a mean particle size of 10-30 microns and less than 10% of the particles of said at least one active agent with a mean particle size equal to or below 5 microns, and having the particles of said diluent with a mean particle size of 50-200 microns.

The composition of the embodiment is essentially free of any excipients other than the solid diluent, such as lactose monohydrate or a lactose functional analogue. In another embodiment, a pharmaceutical composition in a form of dry powder for intranasal administration by transmucosal systemic delivery via the upper nose mucosa (the turbinate and lymphoid tissues located at the back of the nasal cavity) of a composition comprises an active agent having a mean particle size in the range of 10-30 microns, wherein at least 90% of its particles have a mean particles size of not less than 5 microns and not more than 30 microns, and a diluent having a mean particle size in the range of 50-200 microns. As noted above, the diluent is also used for preventing aggregation of the dry powder particles containing at least one active agent.

At first sight, it would seem that the larger particle size might lead to a relatively lower N2B bioavailability of the active agent. However, this is offset by the better absorption of the larger particles of the active agent in the present invention, due to the longer residence time of the active on the nasal mucosa. Thus, a double advantage is obtained by administration of the dry powder composition of this specific particle size range: on one hand, better absorption of the active agent, and on the other hand, this mode of administration using delivery of relatively large particles directly to the upper region of the nasal cavity is substantially free of systemic effects due to lung delivery. In a further embodiment, the pharmaceutical composition for intranasal N2B administration comprises an active agent having a particle size in the range from about 10 microns to about 30 microns, and more than 90% particles of the active agent are above 5 microns, and wherein the active agent is delivered to the superior region of the nasal cavity. In yet further embodiment, the composition comprises an active agent having a mean particle size range of 10-30 microns, wherein at least 90% of its particles have a mean particles size of not less than 5 microns and not more than 30 microns, and a diluent with a particle size in the range of 50-200 microns, said composition may be administered either by nose-to-brain (N2B) delivery or by systemic delivery, or both.

In some embodiment, the intranasal delivery method of the present application provides delivery of dry powders to the nasal mucosa, olfactory region, the trigeminal nerve and other structures of the limbic system. In another embodiment, the pharmaceutical composition is used to deliver the active agent to the upper region of the nasal cavities. This upper region represents the only region where it is possible to circumvent the blood-to-brain barrier and enable transport to the cerebrospinal fluid (CSF) and the brain.

The composition of the embodiments may be delivered by any one of the known in the art nasal devices, such as pressurised devices, dry powder sprayers or bi-directional nasal devices. Multi-dose devices as well as single-dose devices may be used.

In some embodiments, the desired attributes for an intranasal powder formulation with commercial potential required in EMA and FDA Guidelines (8) are inherent features of the compositions of the embodiments. The uniform dose deliverability of the initial and stored formulation by a device for intranasal administration is exemplified in Example 22. None of the dose measurements was found to be outside 75-125% of the label claim.

The present application provides an apparatus and a method for the manufacture of a pharmaceutical composition in a form of dry powder for intranasal delivery having less than 5% of small particles below 5 microns, to exclude undesirable administration to the lungs. FIG. 2 schematically shows the apparatus for the preparation of the pharmaceutical composition of the embodiments in a dry powder form, said apparatus comprises the following components:

a) A spray-drying chamber [1] capable of spray-drying a clear and homogeneous solution of at least one active agent to obtain dry powder particles of said at least one active agent in a moist air, said solution being free of diluent;
b) A cyclone separator [2] capable of receiving said dry powder particles and the moist air stream from said spray-drying chamber [1], separating said particles from the moist air through vortex separation, exhausting the air and transferring the separated particles to a receiving chamber [3] through a bag filter; and
c) The receiving chamber [3] (or "receiver") pre-filled with a diluent and adapted for receiving the separated dry powder particles from the cyclone separator [2], mechanically stirring and homogenising said particles with the diluent to obtain the pharmaceutical composition in the dry powder form of the embodiments; wherein said diluent is capable of colliding and continuous in-situ blending with the particles during the stirring in the receiving chamber [3], thereby preventing their aggregation and preserving their original size and shape.

The spray-drying chamber is equipped with nozzles, which are used to produce droplets of the active agent solution, to control the droplet and powder particle size and to maximise heat transfer and the rate of solvent vaporisation. The spray-dryer apparatus of the embodiments thus receives a stream of the liquid solution containing the active agent, sprays it through the nozzles into a hot gas stream, such as nitrogen or air, and removes the solvent as a vapor. As the moisture quickly leaves the droplets, the dry powder is produced. The droplet size may range from 20 to 180 μm, depending on a particular nozzle used. In the present embodiments, the sprayed solution of the active agent is free of any diluent.

The nozzles are designed to spray the solution of the active agent into a hot air flow, thereby achieving a thorough mixing and uniform distribution of the hot air flow and sprayed solution in the spray-drying chamber to produce a substantially complete evaporation of liquids and drying of solid particles of the active agent from the mixture throughout said chamber. In a specific embodiment, the spray-drying chamber is equipped with a two-fluid nozzle having an appropriate opening controlling the API particles size in the range of 10-30 µm. One of the fluids is an active agent solution, free of any diluent, and the other fluid is a drying gas or air.

At the laboratory scale, the stirring and homogenisation is achieved by using a magnetic stirrer and a magnetic bar of appropriate size, in addition to the rotation of the receiving chamber. At industrial scale, the stirring and homogenisation may be achieved by using a mechanical stirrer of appropriate size and form, or moving, rotation and vibration of the whole receiving chamber. A conventional spray-drying apparatus contains the empty receiving chamber collecting the dry powder particles of an active agent. This receiver is emptied from time to time in order to ensure the continuous process. In contrast, the present application discloses the receiving chamber pre-filled with a continuously stirred diluent for preventing aggregation of the dry powder particles and preserving their original size and shape.

The method for the preparation of the pharmaceutical composition of the embodiments in a dry powder form is based on the spray-drying process rapidly drying the solution of at least one active agent, free of any diluent or excipient, with hot air, thereby producing a dry powder of the active agent. This method comprises the following steps:

A. Preparing a clear and homogeneous solution of at least one active agent in an organic solvent or solvent mixture, in a solvent-water or water miscible solvent mixture, or in water.

B. Filling the receiving chamber with a diluent and continuously stirring the diluent in the receiving chamber;

C. Streaming the solution prepared in step (A) together with hot gas to the spray-draying chamber, spray-drying the solution in the spray-drying chamber to obtain dry powder particles of said at least one active agent in a moist gas, and transferring the obtained dry powder particles and the moist gas stream to the cyclone separator;

D. Separating said particles from the moist gas through vortex separation in the cyclone separator, exhausting the gas and transferring the separated particles to the receiving chamber through a bag filter;

E. Stirring and homogenising said particles received from step (D) with the diluent in the receiving chamber to obtain the pharmaceutical composition of the embodiments in the dry powder form; wherein said diluent is capable of colliding and continuous in-situ blending with the particles during the stirring in the receiving chamber, thereby preventing their aggregation and preserving their original size and shape; and F. Adding diluent and additionally mixing of the pharmaceutical composition obtained in step (E) with the additional amount of the diluent to achieve the desired active agent-to-diluent ratio in said pharmaceutical composition.

The gas used in the spray-drying process is normally air. However, if the solvent is flammable, for example ethanol, or the product is oxygen-sensitive, then nitrogen or any other suitable inert gas may be used instead.

In a particular embodiment, the clear and homogeneous solution of the active agent is obtained by dissolving an active agent either as a free base or as a salt in an organic solvent, a mixture of two or more organic solvents or in water. The gas outlet temperature in the method of the embodiments is generally about 75° C. or below, preferably about 70° C. or below, more preferably about 59° C. or below, yet more preferably about 52° C. or below, or about 50° C. The gas inlet temperature is generally about 75° C. or higher, preferably about 80° C. or higher, more preferably about 90° C. or higher, yet more preferably about 100° C. or higher, even more preferably about 110° C. or higher, or about 120° C. The volatile products obtained in the process are the organic solvents and/or water. The volume of water should be 50% or more of the volume of the volatiles. In the specific embodiment, a Class 3 organic solvent is used in the method for the preparation of the pharmaceutical composition in a dry powder form. The residual solvent content after drying is less than 0.5%.

The drug (active agent) content of the composition of the embodiments may be adjusted so as to provide the total dose of the drug required to achieve the therapeutic effect as a single dose in a single nostril. The drug administration can be repeated in the second nostril in order to double the amount of the active material. Stability of the composition of the embodiments on storage was determined under accelerated and ambient conditions.

The device used for the intranasal delivery of the compositions of the embodiments may be engineered so as to provide the appropriate plume geometry and spray pattern of initial and stored compositions. In some embodiments, these compositions may have a narrow particle size distribution with median diameter between 10 to 20 microns.

Figure 8A:
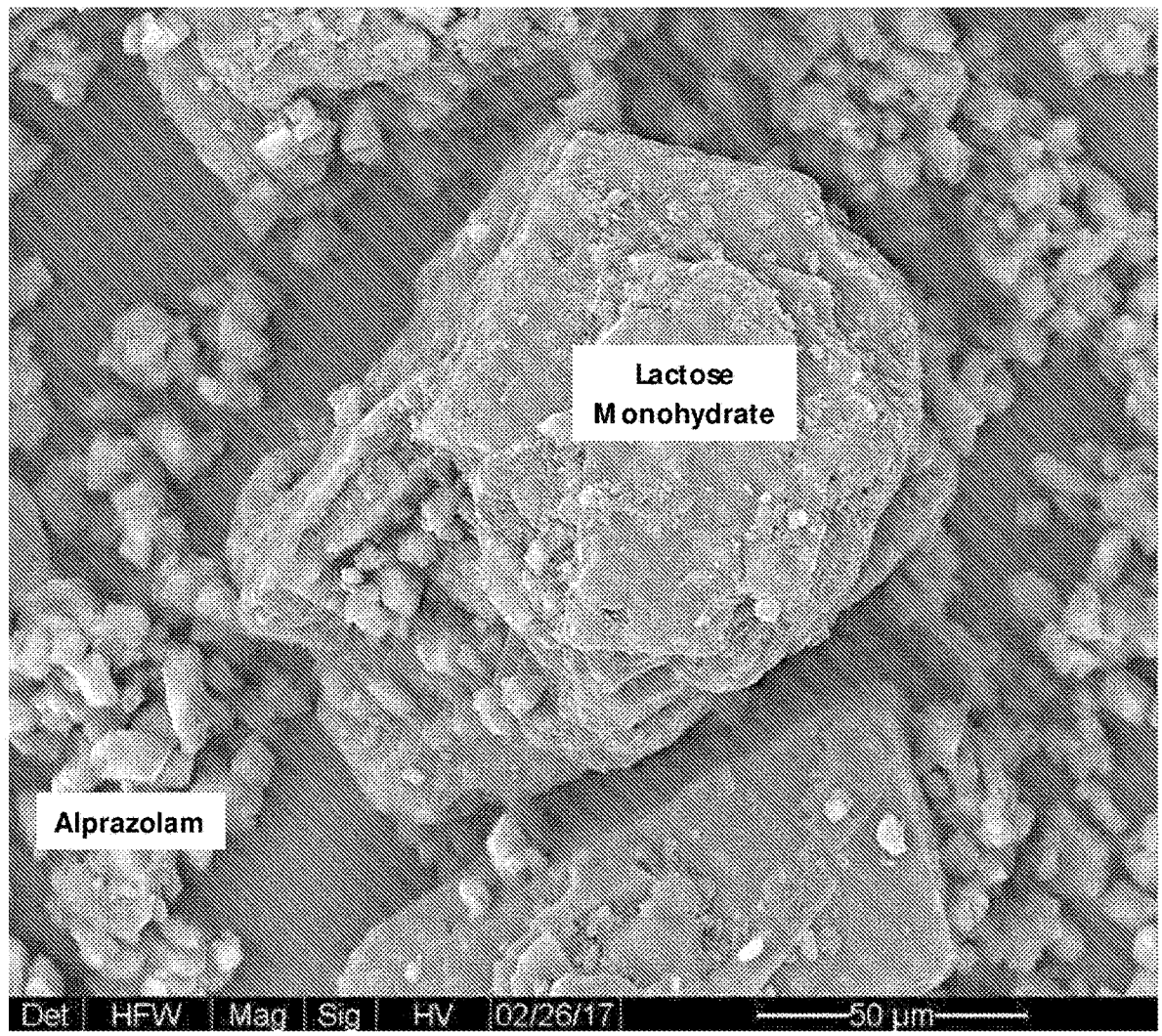
FIG. 8a shows the SEM image (×1200) of lactose monohydrate (large polyhedrons) and alprazolam (small polyhedrons) of the dry powder composition of the embodiments for nasal administration formulation.
Figure 8B:
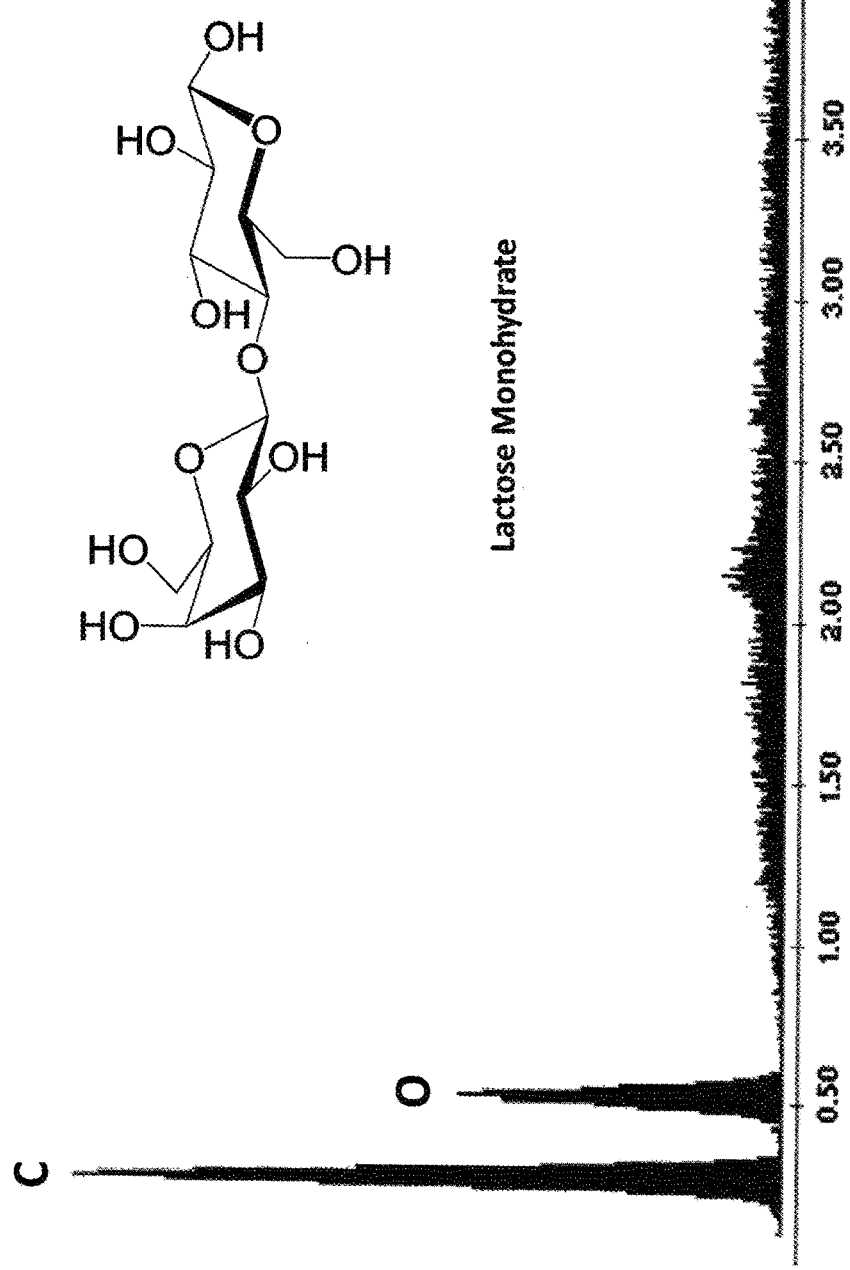
FIG. 8b shows the X-ray elemental analysis of the large polyhedrons confirming that these are the particles of lactose monohydrate containing "C" and "O" atoms.
Figure 8C:
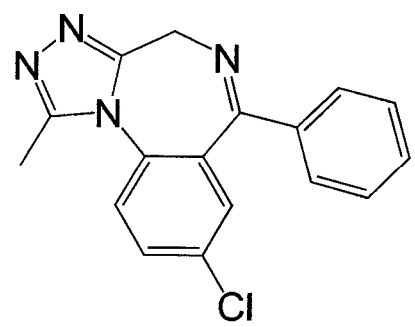
FIG. 8c shows the X-ray elemental analysis of the small polyhedrons confirming that these are the particles of alprazolam containing "C", "O" and "Cl" atoms.
Figure 8C:
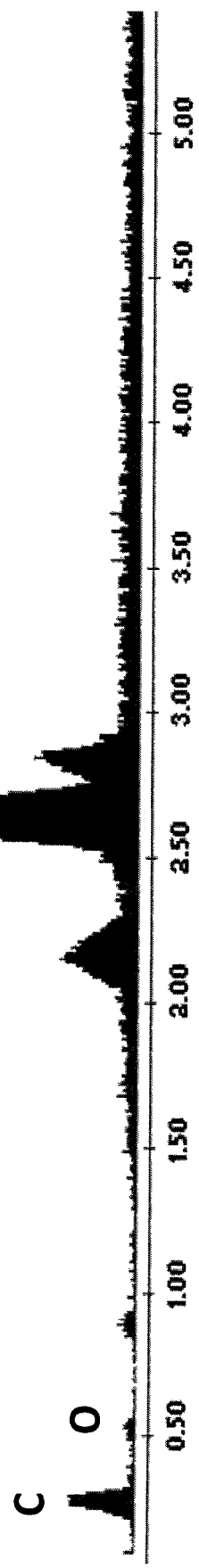

The shape and particle morphology of the dry powder of the embodiments for intranasal delivery were characterized using an electron microscope. Reference is now made to FIGS. 8a-8c and Example 13 (in the experimental section below) showing the polyhedron shape of the particles. FIGS. 3, 4, 9 and 11 show spherical particles, contribution of which may be more significant in reaching the deeper region of the nasal passage.

The process of the embodiments for the preparation of the pharmaceutical composition of the present embodiments in a dry powder form for nasal delivery produces preponderantly a spherical population of particles. In rare cases, the active agent may form a polyhedron-shape crystalline particles or spherical/polyhedron mixtures.

Many previous attempts at developing an intranasal powder formulation fell short in one or several of the desired properties including satisfactory safety and tolerability profile. The compositions of the embodiments are designed to have some or all of these desired properties. These compositions have two required components:

(a) The active agent may be hydrophilic or lipophilic active agent, wherein the hydrophilic active ingredient may be delivered via olfactory mucosa to the brain and the lipophilic active agent may be delivered via nasal mucosa to systemic circulation and then to the brain, by-passing the liver.

(b) Lactose monohydrate or a lactose monohydrate functional analogue also used for preventing aggregation of the active agent particles and preserving their original size and shape.

The active agent of the embodiments is a hydrophilic or lipophilic, chemical or biochemical, solid therapeutic substance selected from compounds for use in common cold treatment, anti-addiction agents, anti-infective agents, analgesics, anaesthetics, anorexics, antiarthritics, anti-allergy agents, antiasthmatic agents, anticonvulsants, anti-depressants, antidiabetic agents, anti-depressants, anti-diuretics, anti-emetics, antihistamines, anti-hypertensive agents, anti-inflammatory agents, antimigraine preparations, anti-motion sickness preparations, antinauseants, antineoplastics, antiobesity, antiosteoporosis, anti-Parkinsonism drugs, antipruritics, antipsychotics, antipyretics, anticholinergics, benzodiazepine antagonists, bone stimulating agents, central nervous system stimulants, hormones, hypnotics, immunosuppressants, prostaglandins, proteins, peptides, polypeptides and other macromolecules, psychostimulants, compounds for use in rhinitis treatment, compounds for use in sexual hypofunction treatment, sedatives, compounds for use in treatment of known or suspected opioid overdose, tranquilizers and vitamins, probiotics, natural ingredients, peptide or protein therapeutic agents such as cytokines, hormones, clotting factors, vaccines, monoclonal antibodies, amino acids, or any combination thereof.

In some embodiments, the active agent is selected from sumatriptan succinate, zolmitriptan salts, naratriptan, rizatriptan, almotriptan, eletriptan, frovatriptan, bupivacaine, fibroblast growth factor, cephalexin, lidocaine, clobazame, midazolam, alprazolam, diazepine, lorazepam, dexmedetomidine, monosialoganglioside, cocaine, insulin, glucagon, oxytocin, fentanyl, sulfentanil, diamorphine, ketamine, apomorphine, buprenorphine, morphine sulphate, oxycodone hydrochloride, butorphanol, NSAIDs, paracetamol, benzodiazepines, dopamine, pramipexole, rasagiline, rogitine, ondansetron, granisetron, metoclopramide, naloxone, naltrexone, atropine, adrenaline, cannabis active compounds, epinephrine, isosorbide dinitrate, obitoxine, dexmedetomidine, metochlorpramide, L-dopa, nicotine, sildenafil, nafarelin, dobutarnine, phenylephrine, tramazoline, xylometazoline, tramadol, methacholine, ipratropium, scopolamine, propranolol, verapamil, hydralazine, nitroglycerin, clofilium tosylatecannabis active compounds and pharmaceutically acceptable salts, isomers, and mixtures thereof.

In a specific embodiment, the dry powder of the active agent for nasal delivery contains at least 90% of the particles having a mean particle size of 10-30 microns, and less than 10% of the particles having a mean particle size equal to or below 5 microns. The particle size is measured using the laser diffraction method. The active agent particles may have spherical, ellipsoid, polyhedron, cubic, plate, or needle shapes. The preferable particle shapes are spherical and ellipsoid. These shapes provide the best aerodynamic properties of the active agents. The drug particle shape and morphology is determined using the electron microscopy.

The solid diluent of the embodiments is selected from lactose monohydrate or a lactose monohydrate functional analogue, such as lactose, cellulose and derivatives, starch and derivatives, dextrose, sorbitol, mannitol, maltitol, xylitol or mixtures thereof. The preferred solid diluent is lactose monohydrate.

Lactose may be present in the form of α-lactose monohydrate, anhydrous β-lactose or amorphous lactose. α-Lactose monohydrate is a commonly used DPI (dry powder inhaler) excipient, and is a pharmacopeia excipient for DPIs in a pulmonary delivery route. Lactose monohydrate of the embodiments has a bulk density of 0.6-0.8 g/ml and partly tomahawk-shaped crystals with the following particle size distribution: $D_{10}$ 30-60 μm; $D_{50}$ 70-110 μm and $D_{90}$ 110-150 μm.

According to Jagdeep Shur et al, "*From single excipients to dual excipient platform in dry powder inhaler products*", International Journal of Pharmaceutics (2016), 514, pages 374-383, the single excipient platform (SEP) has been the most prevalent excipient strategy used in many commercial DPI products. The majority of approved SEP DPI products have been developed based on the well-known 'carrier' approach. The role, or functionality, of the single excipient in the SEP-based DPI products has traditionally been described as a 'dispersant', 'filler', 'diluent' or 'carrier'. The 'carrier' description is now so commonplace in academic, industrial and regulatory circles that in 2014 it was incorporated into the updated respiratory section of the United States Pharmacopoeia (General chapter 1059). Such 'carrier' excipients, often of a small particle size, are also used in what are described as 'agglomerate' formulations. This is in contrast to the large particle size (50-200 microns) of lactose or lactose functional analogue of the embodiments. Thus, unlike the regular DPIs, the excipient of the embodiments (such as lactose or lactose functional analogue) has rather large particle size (50-200 microns), and—while being multi-functional, it is mainly used as a diluent and carrier for preventing agglomeration of much smaller particles of an active agent, deagglomeration of the particles and homogenisation of the composition. Therefore, the excipient of the embodiments is referred to throughout the present application as "diluent".

It is a surprising and unexpected finding that the lactose monohydrate solid diluent of the embodiments may serve for preventing aggregation or agglomeration of the active agent particles, or as a disaggregant or de-agglomerating agent in the preparation of the dry powder composition for intranasal administration, when the spray-dried active agent and the diluent are mixed in-situ in the receiving chamber of the spray-drying apparatus. It is indeed unpredictable and surprising that the large particles of lactose monohydrate with a mean diameter of 50-200 μm are capable of preventing the aggregation of the small active agent particles with a mean diameter of 10-30 μm. The lactose monohydrate particles cannot therefore enter the nasal passage and become swallowed after actuation.

Thus, the compositions of the embodiments comprise at least one active agent and a diluent, such as lactose or a lactose functional analogue, and are substantially free of other excipients, such as surfactants, lipid agents, solvents or propellants. Most of the DPI formulations rely on lactose monohydrate as a diluent. However, lactose cannot be used in the compositions comprising active compounds that interact with the reducing sugar function of lactose in the Maillard reaction. Lactose functional analogues of the embodiments, which may be used as a solid diluent instead of lactose and may replace lactose in some compositions, particularly as an alternative for patients suffering from lactose intolerance, are selected from cellulose and derivatives, starch and derivatives, mannitol, glucose, sorbitol, maltitol, xylitol or mixtures thereof. The particle size of these diluents is also in the 50-200 μm range.

The pharmaceutical composition of the embodiments may further comprise one or more pharmaceutically acceptable diluents, excipients or both. The pharmaceutical composition of the embodiments may be prepared in the form of a powder, simple powder mixtures, powder microspheres, coated powder microspheres, liposomal dispersions or combinations thereof.

The conventional spray drying process uses an empty receiving chamber in the beginning of the process. Such receiving chamber is filled with the spray-dried product powder and emptied from time to time in order to ensure the continuous process. In the present embodiments, the receiving chamber is however pre-filled with the continuously stirred diluent for preventing agglomeration or de-agglomeration of the active agent particles. The regular methods for the preparation of dry powders for nasal delivery usually use surfactants and lipid agents for disaggregation and de-agglomeration of the solid particles and for preventing their aggregation. It was surprisingly and unexpectedly found that rather coarse particles of the diluent, such as lactose or lactose functional analogue, with the size range of 50-100 µm prevent aggregation of the active agent particles having the size range of 10-30 µm. In a further embodiment, a method for disaggregation and de-agglomeration of the active agent dry powder and for preventing its solid particles aggregation comprises in-situ mechanical mixing of the agent dry powder with a diluent, preferably lactose monohydrate, in the receiving chamber of the spray-drying apparatus of the embodiments.

The active agent for nasal inhalation in a dry powder form is usually produced by jet or wet milling techniques that give rise to broad particle size distribution and to non-spherical and non-uniform shapes of the particles. In addition, the jet or wet milling methods produce particles of less than 5 µm. These coarse inhalable particles of less than 5 µm may easily reach the lungs by nasal spraying (with a nasal spraying device) or by inhaling (with an inhalation device) and cause tiny wounds and scarring to the lungs: each time this happens, it causes a very small amount of irreversible damage. The immediate effect is unnoticeable, but over some periods of time, this can result in significantly decreased lung capacity, and a number of other health issues. Therefore, production of the dry powder particles ranging from 2-10 µm, particularly less than 5 µm, for the intranasal administration should be avoided by all means. The present application provides solution also to this problem by disclosing the method for the preparation of the active agent particles of the embodiments having a spherical shape with a narrow size distribution (10-30 µm), which are safe for use in nasal spraying or inhaler devices.

In some embodiments, there is provided a mode of administration of an active agent by nasal delivery, wherein the active agent has a particle size more than 10 µm and a narrow size distribution range, the particles are substantially spherical or ellipsoid and the composition comprising this active agent is administered by a spraying with a nasal spraying device or inhaling with an inhaler device.

As described above, the preparation method of the embodiments is characterised by the two major steps: the drying, more preferably spray-drying, of the active agent clear and homogeneous solution, and then mixing the obtained dry powder with the solid diluent, such as lactose or lactose functional analogue, thereby obtaining the composition of the embodiments in a form of dry powder consisting of an active agent and a solid diluent, said composition having a particle size ranging from 10 to 30 µm and a spherical shape of the drug particle. This is in contrast to spray-drying processes described in the patent documents U.S. Pat. No. 6,462,090, US 20080292713, US 20150010633 and US 20160354288, which yield the composite active agent particles with the particle size less than 5 µm. The spray-drying step in the process of the embodiments yields active agent particles larger than 10 µm. These particles are then in-situ blended with the solid diluent, such as lactose, to prevent the growth of the particles and their agglomeration.

The compositions of the embodiments for intranasal administration containing the active compounds, such as analgesics, opioids or triptans may be used for the fast and efficient pain relief.

To sum up, in some embodiments, there is provided a pharmaceutical composition, wherein the solid diluent is the only excipient, said solid diluent is used for prevention of active agent aggregation in said composition. In some embodiments, there is provided a pharmaceutical composition, wherein the dry powder particles of the active agent are substantially in a spherical form. In some embodiments, a therapeutically effective dose of the pharmaceutical composition of the embodiments may be intranasally administered to a patient in need thereof, wherein the administration is targeted at the uppermost region of the nasal cavity, thereby resulting in the nose-to-brain (N2B) delivery of the active agent to the brain of the patient, or in the transmucosal systemic administration. In some embodiments, there is provided a method of treatment, wherein the administration delivers an entire therapeutically effective dose of at least one active agent to one nostril. In some embodiments, there is provided a method of treatment, wherein the therapeutically effective dose of at least one active agent is administered once daily. In some embodiments, there is provided a method of treatment, wherein the therapeutically effective dose of at least one active agent is lower than the therapeutically effective dose of a similar intranasal composition using a non-N2B mode of delivery.

Figure 14:
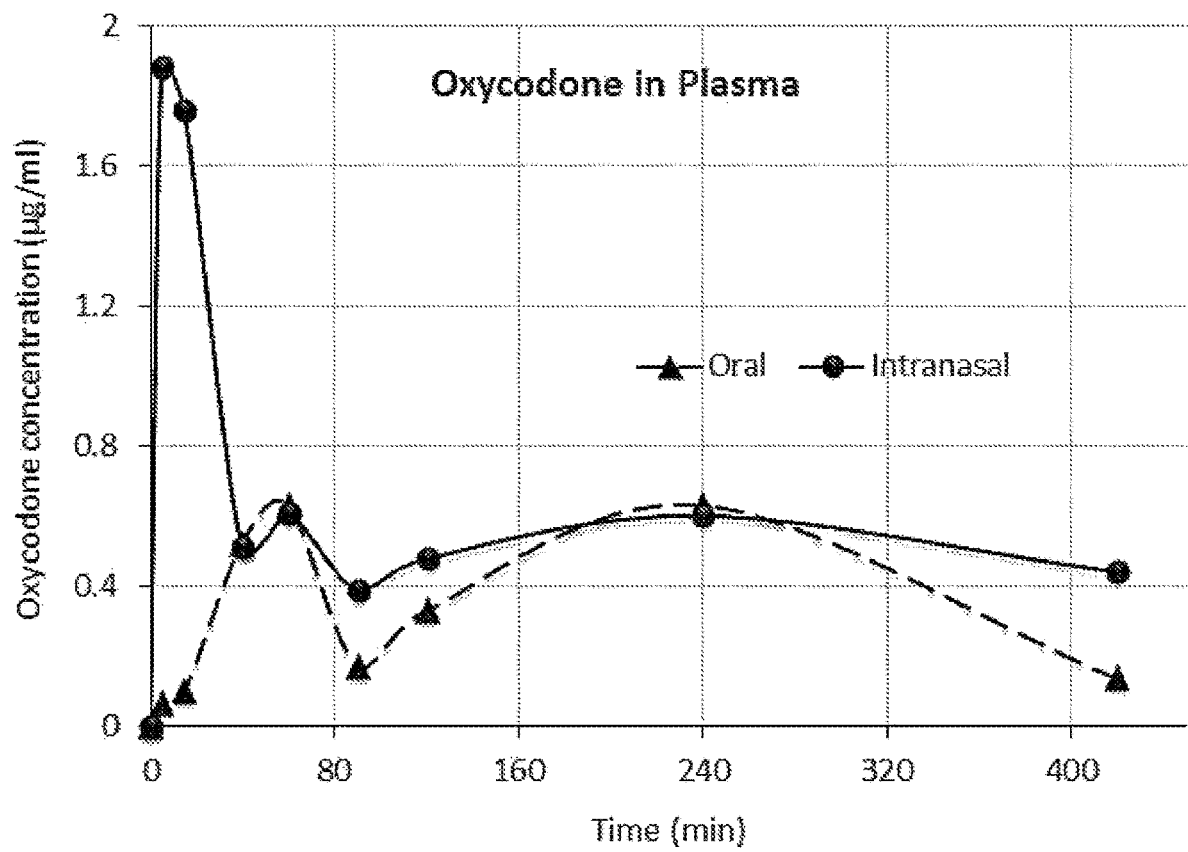
FIG. 14 shows the oxycodone pharmacokinetic profiles in rat's plasma following administration of oral gavage (oral) and intranasal powder (intranasal) to 12 SD rats at dose of 10 mg/kg.
Figure 15:
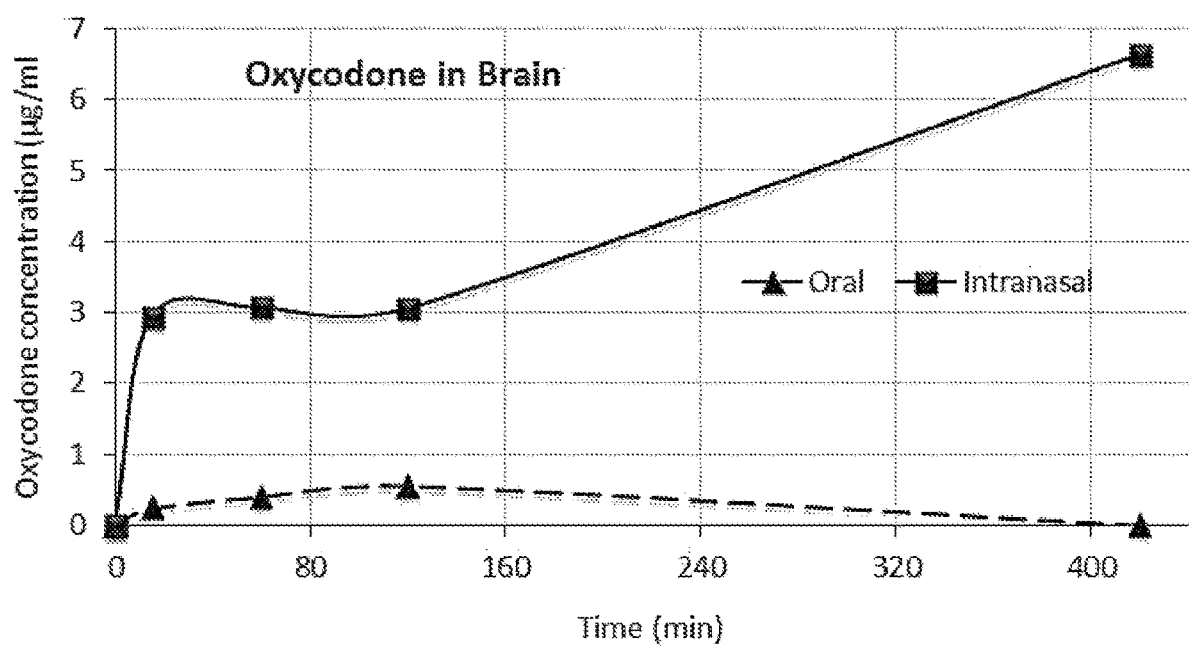
FIG. 15 shows the oxycodone pharmacokinetic profiles in rat's brains following administration of oral gavage (oral) and intranasal powder (intranasal) to 12 SD rats at dose of 10 mg/kg.

The significantly improved pharmacokinetic profile and superior effects of the intranasal composition of the present invention on the brain and plasma compared to the oral solution are shown in the in-vivo experiments (see Example 24, and FIGS. 14-15). The faster onset of action and higher drug concentration in plasma were demonstrated for the intranasal powdered composition of the present invention compared to the oral solution. In addition, the faster onset of action and higher sustained drug concentration in brain was demonstrated for the intranasal powdered composition of the present invention compared to the oral solution.

In particular and specific embodiments, the present disclosure provides methods and drug delivery devices (as used and disclosed herein) for treating overdoses opioid/s as defined herein, by intranasal administration to a patient in need of a composition according to the present disclosure. In embodiments of the presently disclosed methods, administration can be into one or both nostrils of the patient.

The administration of the opioid antagonist, specifically naloxone, leads to titrating opioid receptor occupancy, and thus the presently disclosed methods can be used for titrating opioid receptor occupancy. The presently disclosed methods of treating opiate overdose, can lead to complete reversal of an opioid overdose.

Further disclosed herein are methods for lowering opioid overdose risk in a subject at risk for opioid overdose. In these methods, the presently disclosed composition, particularly naloxone composition is provided to the subject at risk for opioid overdose together with a therapeutically effective amount of an opioid agonist. Thus, the opioid receptor antagonist, specifically naloxone, is administered at a therapeutically effective amount together with a therapeutically effective amount of the opioid agonist, for example morphine, or other, as listed above. The opioid receptor agonist and the opioid/opiate, can be administered simultaneously or sequentially. For example, the opioid receptor agonist and the opioid/opiate can be contained in a drug device as disclosed herein, in different compartments, that can be actuated by same or different mechanism. In some embodiments, methods of treatment according to the present disclosure can comprise intranasally administering to a subject in need thereof therapeutically effective amounts of a short-acting opioid antagonist, such as naloxone or naltrexone, and a long-acting opioid antagonist, such as for example nalmefene.

The presently disclosed compositions, drug devices thereof, methods of treatment and kits can be used also for treating opioid overdose symptoms. The opioid receptor antagonist, specifically naloxone, prevents or partially or completely reverses the effects of opioids respiratory depression, postoperative opioid respiratory depression, altered level consciousness, miotic pupils, cardiovascular depression, hypoxemia, acute lung injury, aspiration pneumonia, sedation, and hypotension. In some embodiments, the respiratory depression is caused by illicit use of opioids or by an accidental misuse of opioids during medical opioid therapy. Also, the opioid receptor antagonist compositions of the present invention, specifically naloxone compositions as defines herein, can reverse adverse effects various drugs that are agonist-antagonists of opioid receptors, such as pentazocine, tramadol, buprenorphine and others. In some embodiments the patient is not breathing.

With specific regard to naloxone and its pharmaceutically acceptable salts, an overdose of naloxone has not been reported in humans, notwithstanding some side effects, such as Although naloxone may have some side effects such as increased blood pressure and cardiac arrest, as well as some others. Therefore, the presently disclosed compositions, dose devices thereof and methods thereof, can be used in preventing complications from severe opioid withdrawal. The methods comprise intranasal administration of a dose of the naloxone composition of the present disclosure.

Naloxone powder compositions according to the present disclosure can be initially use by single dose administration, as described herein, followed by monitoring the treated subject's relevant medical indices, such as blood pressure, breathing, etc. If the desired degree of counteraction and improvement in respiratory functions is not obtained, administration may be repeated at 2 to 3 minute intervals. If no response is observed after administration of about 8-10 mg of naloxone, the diagnosis of narcotic-induced overdose should be assessed.

Accordingly, also provided herein are methods of treating opioid overdose or a symptom thereof, comprising intranasally administering to a subject in need thereof a therapeutically effective amount of an opioid antagonist, specifically naloxone and pharmaceutically acceptable salts thereof such as naloxone hydrochloride or hydrate thereof, wherein the therapeutically effective amount is equivalent, for example to about 0.5-15 mg, more specifically about 2-12 mg and any suitable sub-range thereof of naloxone hydrochloride or a hydrate thereof. One single dose unit specifically starts with 1.5 mg, 2 mg, 4 mg, up to a cumulative dose of 12-15 in multiple administrations.

In all aspects and embodiments of the present disclosure the therapeutically effective therapeutically effective amount of the opioid antagonist, specifically naloxone and its pharmaceutically acceptable salts, such as but not limited to naloxone hydrochloride or hydrate thereof, is equivalent to about 4 mg, administered intranasally as a single dose, to about 12 mg or 24 mg of naloxone hydrochloride, optionally administered in several doses. In some embodiments, the therapeutically effective amount is equivalent to about 3, 4, 5, 6, 7, or 8 to about 9, 10, 11, 12, or 13 mg, respectively, of naloxone hydrochloride. In some embodiments, the opioid antagonist is the only pharmaceutically active compound in pharmaceutical composition. In some embodiments, the opioid antagonist is naloxone hydrochloride. In some embodiments, the opioid antagonist is anhydrous naloxone hydrochloride.

Methods of treatment with naloxone or other opioid receptor antagonists powder compositions and formulations according to the present disclosure can provide for a plasma concentration versus time curve of said naloxone hydrochloride in said patient of a $T_{max}$ between about 0.13 and about 0.75 hours, for example $T_{max}$ of 0.25 h.

The methods of treatment with naloxone or other opioid receptor antagonists powder compositions and formulations according to the present disclosure can provide mean maximum plasma concentration of naloxone of about 11.8 ng/mL within 15 minutes of administration.

Further, treatment by intranasal administration of naloxone or other opioid receptor antagonists powder compositions/formulations according to the present disclosure provides for a high share of the naloxone particles, respectively other opioid receptor antagonist, comprised in the powder reaching turbinates and olfactory regions, while only a small part of the particles of active agent reaches lower parts of the nasal cavity and less than 15 of the particles reach breathing airways and the lungs. For example, as shown in Example 34, at least 86% reached the turbinates region, more specifically about 35% were the middle part and 51% in the upper olfactory area, with less than 10% of the naloxone particles found in the nose and less than 1% reaching the lungs. This provides for improved efficacy of the disclosed powder compositions, with the majority of the active agent reaching nasal mucosa and being absorbed shortly after administration.

EXAMPLES

The following examples illustrate certain features of the present invention but are not intended to limit the scope of the present invention. In the examples below, the term "ratio" refers to the weight/weight ratio, except the cases where use of other units is specifically referred to in the text.

Materials

Sumatriptan succinate (from SMS); lactose monohydrate (from Meggle Pharma); morphine sulphate and oxycodone hydrochloride (from Noramco); naloxone hydrochloride (from Cilag and Noramco); acetaminophen (from Greenville Plant); cannabidiol (from THC Pharm); alprazolam (from Centaur); dopamine hydrochloride and insulin (from Sigma-Aldrich); pramipexole dihydrochloride (from LGM Pharma); ondansetron hydrochloride (from Teva), ethanol and acetone (from BioLab).

Methods

The spray-drying process was carried out using the Mini Spray Dryer B-290 of Büchi Labortechnik AG. A magnetic stirrer (Fried Electric) was placed under the receiver (receiving chamber), a magnetic bar of appropriate size was inserted into the receiver, and then the diluent was added. The liquid feed containing at least one active agent was prepared by dissolving at least one active compound in the selected solvent or mixture of solvents. Quantification was performed using HPLC and a Dionex HPLC instrument. A FEI Quanta-200 Scanning Electron Microscope (SEM) equipped with an Everhart-Thornley Detector was used to obtain the images of the spray-dried powder. The accelerating voltage of 20 kV was applied to provide magnification from 250 to 10,000 times. In addition, an X-ray Element Analysis Detector (Link ISIS, Oxford Instruments, GB) was used to determine the drug and particle identity and their distribution throughout DPI. Particle size was measured using the Malvern Mastersizer 3000 series based on the Light Diffraction method.

Oxycodone assay in the compositions was performed using Dionex HPLC-PDA instrument equipped with Chromeleon software. Column: Agilent, ZORBAX SB-CN 4.6×250 mm, 5µ. Mobile phase: 50 mM potassium dihydrogen phosphate buffer (pH 3.0): acetonitrile (40:60%, v/v). Flow rate: 1.0 mL/min. Column temperature: 25° C. Injection volume: 10 µL.

Oxycodone bio-assay in rat's plasma and brain was performed using Dionex HPLC-PDA instrument equipped with Chromeleon software. Detector: UV at 210 nm. RT of oxycodone: about 2.6 min. Diluent: water standard and sample final concentration about 4 μg/mL. Column: Agilent, ZORBAX SB-CN 4.6×250 mm, 5μ. Gradient: mobile phase A: 50 mM potassium dihydrogen phosphate buffer (pH 3.0): acetonitrile (45:10%, v/v); mobile phase B: acetonitrile. Flow rate: 1.0 mL/min. Column temperature: 25° C. Injection volume: 50 μL. Detection: UV at 210 nm. PDA 200-400 nm. Calibration curve: from 0.1 μg/mL to 4 μg/mL prepared by spiking with rat plasma. Quantitative limit: 0.05 μg/mL. Internal standard: alprazolam.

Processing Oxycodone HCl in Rat Plasma

100 μl plasma (serum) spiked with IS mixed with 600 μL of acetonitrile for precipitation protein and centrifuged at 14000 rpm for 10 min. Supernatant was dried under nitrogen and reconstituted with 100 μL potassium dihydrogen phosphate buffer (pH 3.0).

Processing Oxycodone HCl in Rat Brain

Each individual brain tissue was previously weighted and treated by 0.1M perchloric acid and homogenized. Then it was spiked with IS and mixed with 1400 μL of acetonitrile. After centrifugation at 14000 rpm for 10 min, the upper layer was centrifuged again. Supernatant was dried under nitrogen at 40° C. and reconstituted with 100 μL potassium dihydrogen phosphate buffer (pH 3.0).

Example 1: Spray-Drying of Sumatriptan Succinate Solution without Lactose

This is the reference example for the comparison purposes only. Sumatriptan succinate (12.0 g) was dissolved in 100 ml of deionized (DI) water under stirring at 300 rpm. The resultant clear homogeneous solution was spray-dried using a Büchi Mini Spray-Dryer with inlet air temperature of 105° C. and outlet temperature of 62° C., thereby obtaining the dry powder. SEM image (see FIG. 1) showed that the obtained powder was highly aggregated. Large aggregates up to 500 microns (μm) are clearly seen on the image.

Example 2: Modification of the Commercial Büchi Labortechnik AG Spray-Dryer

Figure 2:
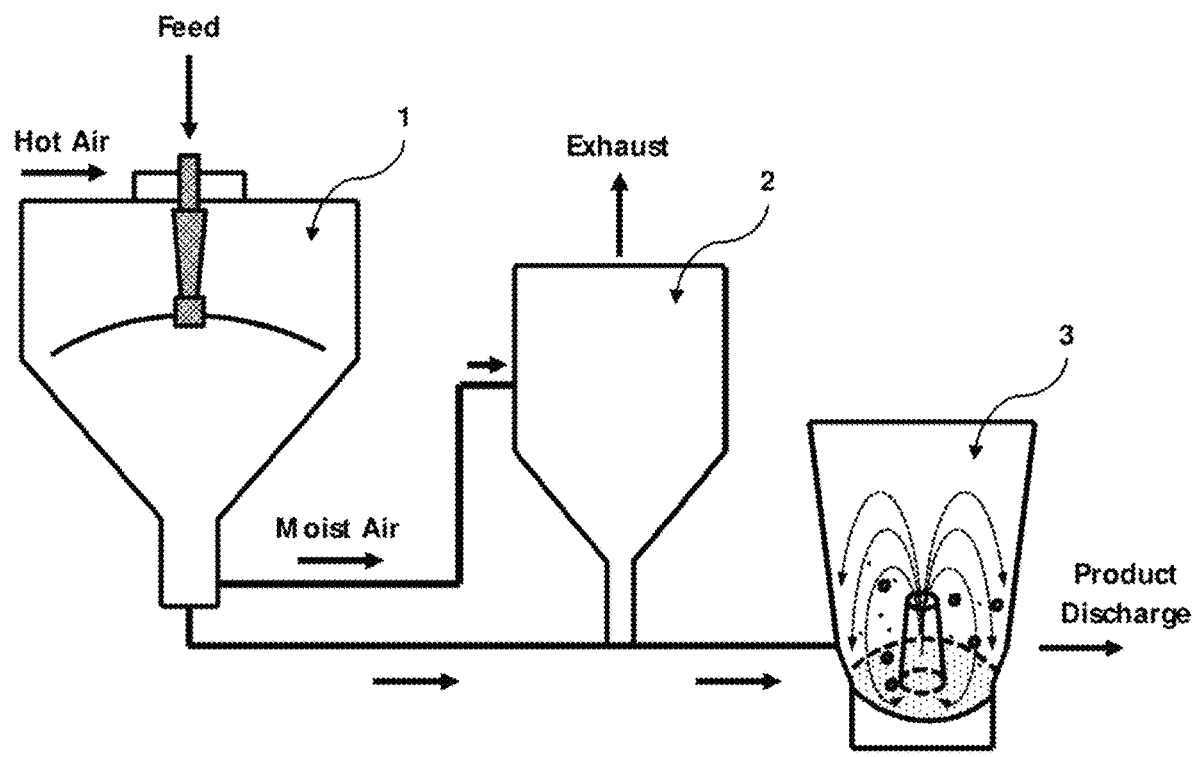
FIG. 2 shows the schematic drawing of the modified spray-dryer apparatus of the embodiments, suitable for the particles engineering and prevention of agglomeration.
Figure 2A:
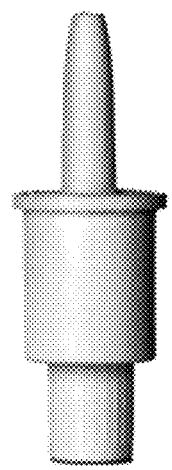
FIG. 2a shows Aptar Unitdose Powder device providing a powder dose volume up to a maximum of 140 mm3, with a dose range between 10-80 mg.

FIG. 2 schematically shows a modified spray dryer of the embodiments. A Mini Spray-Dryer B-290 of Büchi Labortechnik AG was modified by:
1. Addition of a magnetic bar into the glass receiver and placing a magnetic stirrer under the continuously rotating glass receiver of the spray-dryer.
2. Selection of a suitable two-fluids spraying nozzle for spraying the solution containing only an active agent (without diluent) into fine droplets suitable for the preparation of 10-30 μm dry powder particles of the active agent. One of the fluids is the clear and homogeneous solution of the active agent, and the second fluid is the drying gas.

Example 3: Sumatriptan Succinate Composition with Lactose Monohydrate

Sumatriptan succinate (2.3 g) was dissolved in a mixture of acetone (12 g) and ethanol (12 g) under stirring at 300 rpm. An appropriate size magnetic bar was placed in the receiver and lactose monohydrate (2.3 g) was added there. The stirring rate was set at 150 rpm. The clear and homogeneous solution of the active agent (sumatriptan succinate) was spray-dried using the Büchi Mini Spray-Dryer with inlet air temperature of 60° C. and outlet temperature of 55° C., thereby obtaining the dry powder of the active agent, which was further blended with lactose monohydrate in-situ in the receiver. Stirring was being maintained during the entire process. The actual weight of sumatriptan as an active agent in the obtained sumatriptan/lactose composition was 15.4%. The composition was then mixed with an additional amount of lactose in order to reach the required 10% active agent (sumatriptan) concentration.

Example 4: SEM Imaging of the Sumatriptan Succinate Composition

Figure 3:
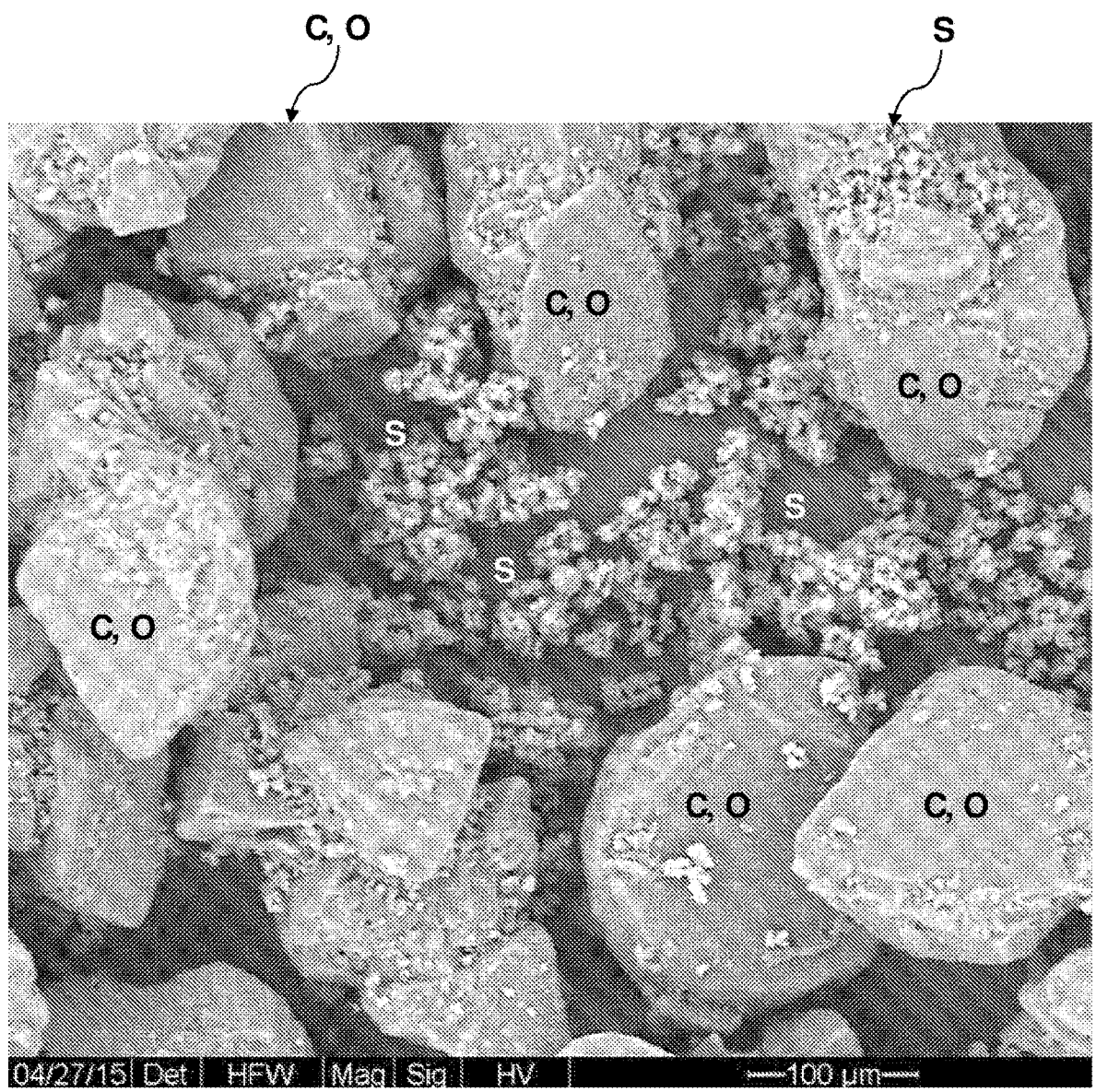
FIGS. 3 and 4 show the SEM images of lactose monohydrate (large cubic particles or tomohawks comprising "C" and "O" elements) and sumatriptan succinate particles (small spherical particles comprising also "S" element) of dry powder for intranasal delivery formulation.
Figure 4:
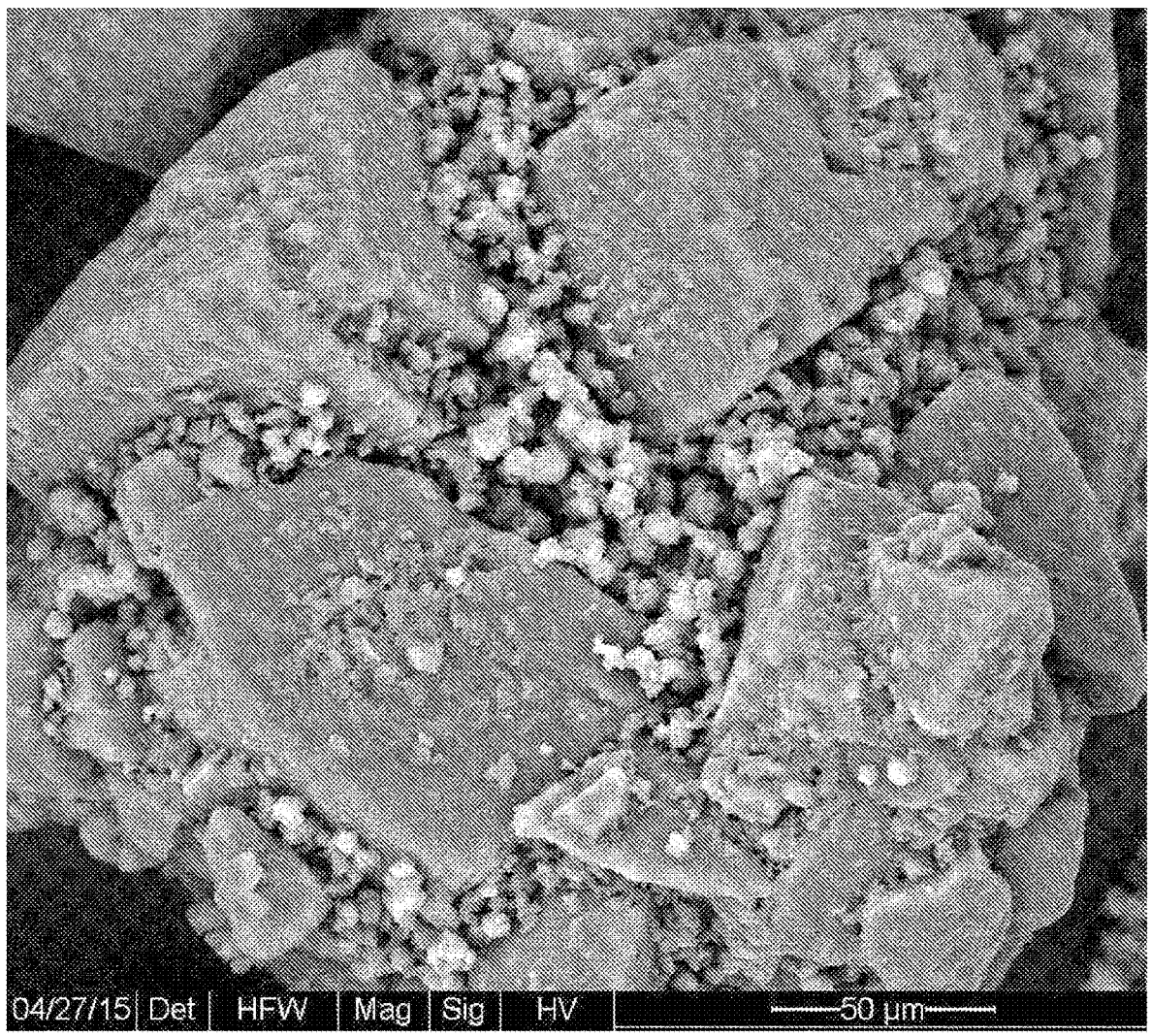

High resolution SEM imaging coupled with an X-ray Element Analysis Detector provides the unique opportunity to identify each individual particle of a formulation by its chemical content. Using this technique, the particles of sumatriptan succinate containing sulphur (S) atoms can be differentiated from lactose particles containing carbon (C) and oxygen (O) atoms (without sulphur). FIGS. 3 and 4 show the small spherical API particles having a narrow size distribution ranging from 5 μm to 20 μm, which are dispersed between large lactose polyhedron particles of ranging from 50 μm to 200 μm. FIG. 3 shows the high-resolution image with the 100-μm bar and the elemental analysis of the particles. FIG. 4 shows the high-resolution image with the 50-μm bar.

Example 5: Particle Size Analysis of the Sumatriptan Succinate Composition

Figure 5:
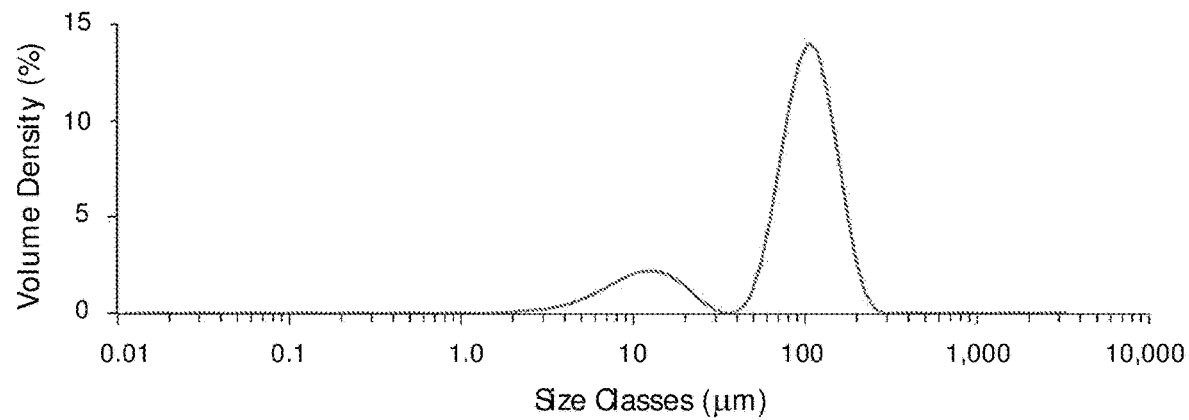
FIG. 5 shows the particle size distribution of the pharmaceutical composition of the embodiments (see Example 3). Two populations of the particles are clearly seen: the active agent (API) in the range of 5-25 microns (m) and lactose in the range of 50-200 microns; D(10)=11.6 µm; D(50)=95.4 µm; D(90)=155 µm.
Figure 6:
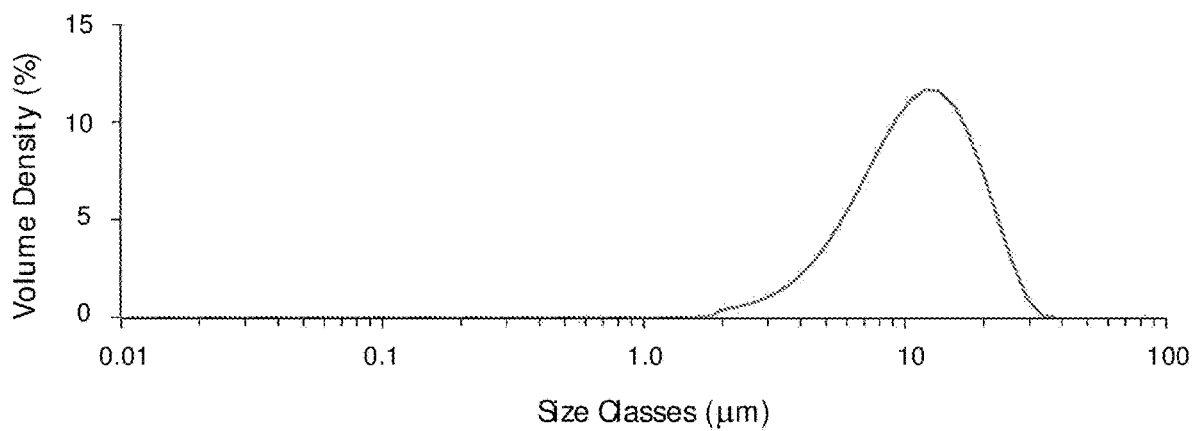
FIG. 6 shows the particle size distribution of the API in the pharmaceutical composition of the embodiments (see Example 3). The mean particles size is 12 µm.

The sumatriptan succinate composition prepared in Example 3 was subjected to the particle size analysis using the Malvern Laser Diffraction instrument (see FIGS. 5 and 6). The following particle size distribution was obtained for the sumatriptan succinate composition (see FIG. 5): D(10)= 7 μm, D(50)=79 μm and D(90)=179 μm. Two populations of the particles are clearly seen in the Figures. The 5-25 μm particles are sumatriptane succinate and the 50-200 μm particles are lactose monohydrate. The amount of the particles having the size less than 5 μm is about 1%. The particle size distribution of sumatriptan succinate alone was estimated in the range of 0-40 μm (see FIG. 6), and the following results were obtained: D(10)=5.2 μm, D(50)=11.2 μm, D(90)=20.1 μm and D(99)=27.1 μm.

Example 6: Acetaminophen (Paracetamol) Composition with Lactose Monohydrate

Acetaminophen (paracetamol) (2.3 g) was dissolved in 65 g ethanol under stirring at 300 rpm. An appropriate size magnetic bar was placed in the receiver and lactose monohydrate (2.3 g) was added there. The stirring rate was set at 150 rpm. The clear and homogeneous solution of the drug was spray-dried using the Büchi Mini Spray-Dryer with inlet air temperature of 105° C. and outlet temperature of 56° C., thereby obtaining the dry powder of paracetamol, which was further blended in-situ with lactose monohydrate. Stirring was being maintained during the entire process. Concentration of paracetamol in the composition was found to be 23% w/w.

Example 7: SEM Imaging of the Paracetamol Composition

The SEM images (not shown here) show that the small spherical particles of paracetamol having a narrow size distribution of 2-30 μm are dispersed between the large polyhedron particles of lactose ranging from 50 μm to 200 μm.

Example 8: Particle Size Analysis of the Paracetamol Composition

The paracetamol composition prepared in Example 6 was subjected to the particle size analysis using the Malvern Laser Diffraction instrument. The following particle size distribution was obtained: D(10)=11.6 μm, D(50)=95.4 μm and D(90)=155 μm. Two separate populations of the particles were clearly seen. The 2-30 μm particles are paracetamol and the 50-200 μm particles are lactose monohydrate. The percentage of the particles having the size less than 5 μm was about 7% w/w.

Example 9: Morphine Sulphate Composition with Lactose Monohydrate

Morphine sulphate (2.3 g) was dissolved in a mixture of 18.9 g ethanol and 13.9 g water under stirring at 300 rpm. An appropriate size magnetic bar was placed in the receiver and lactose monohydrate (2.3 g) was added there. The stirring rate was set at 150 rpm. The clear and homogeneous solution of the active agent was spray-dried using the Büchi Mini Spray-Dryer with inlet air temperature of 110° C. and outlet temperature of 86° C., thereby obtaining the dry powder of morphine sulphate, which was further blended in-situ with lactose monohydrate in the receiver. Stirring was being maintained during the entire process. Concentration of morphine sulphate in the composition was about 32% w/w and concentration of morphine base was about 28% w/w.

Example 10: Particle Size Analysis of the Morphine Sulphate Composition

The morphine sulphate composition prepared in Example 9 was subjected to the particle size analysis using the Malvern Laser Diffraction instrument. The following particle size distribution was obtained: D(10)=7.1 μm, D(50)= 70.7 μm and D(90)=156 μm. The amount of the particles having the size less than 5 μm was about 6.6% w/w.

Example 11: Alprazolam Composition with Lactose Monohydrate

Alprazolam (2.3 g) was dissolved in 32.5 g of ethanol under stirring at 300 rpm. An appropriate size magnetic bar was placed in the receiver and lactose monohydrate (2.3 g) was added there. The stirring rate was set at 150 rpm. The obtained clear and homogeneous solution of the drug was then spray-dried using the Büchi Mini Spray-Dryer with inlet air temperature of 110° C. and outlet temperature of 86° C., thereby obtaining the dry powder of alprazolam, which was further blended in-situ with lactose monohydrate in the receiver. Stirring was being maintained during the entire process. Concentration of alprazolam in the composition was about 33% w/w.

Example 12: Particle Size Analysis of the Alprazolam Composition

The alprazolam—composition prepared in Example 11 was subjected to the particle size analysis using the Malvern Laser Diffraction instrument. The following particle size distribution was obtained: D(10)=11.7 μm, D(50)=88.0 μm and D(90)=187 μm. The amount of the particles having the size less than 5 μm was about 0.6% w/w.

Example 13: SEM Imaging of the Alprazolam Composition

Figure 7:
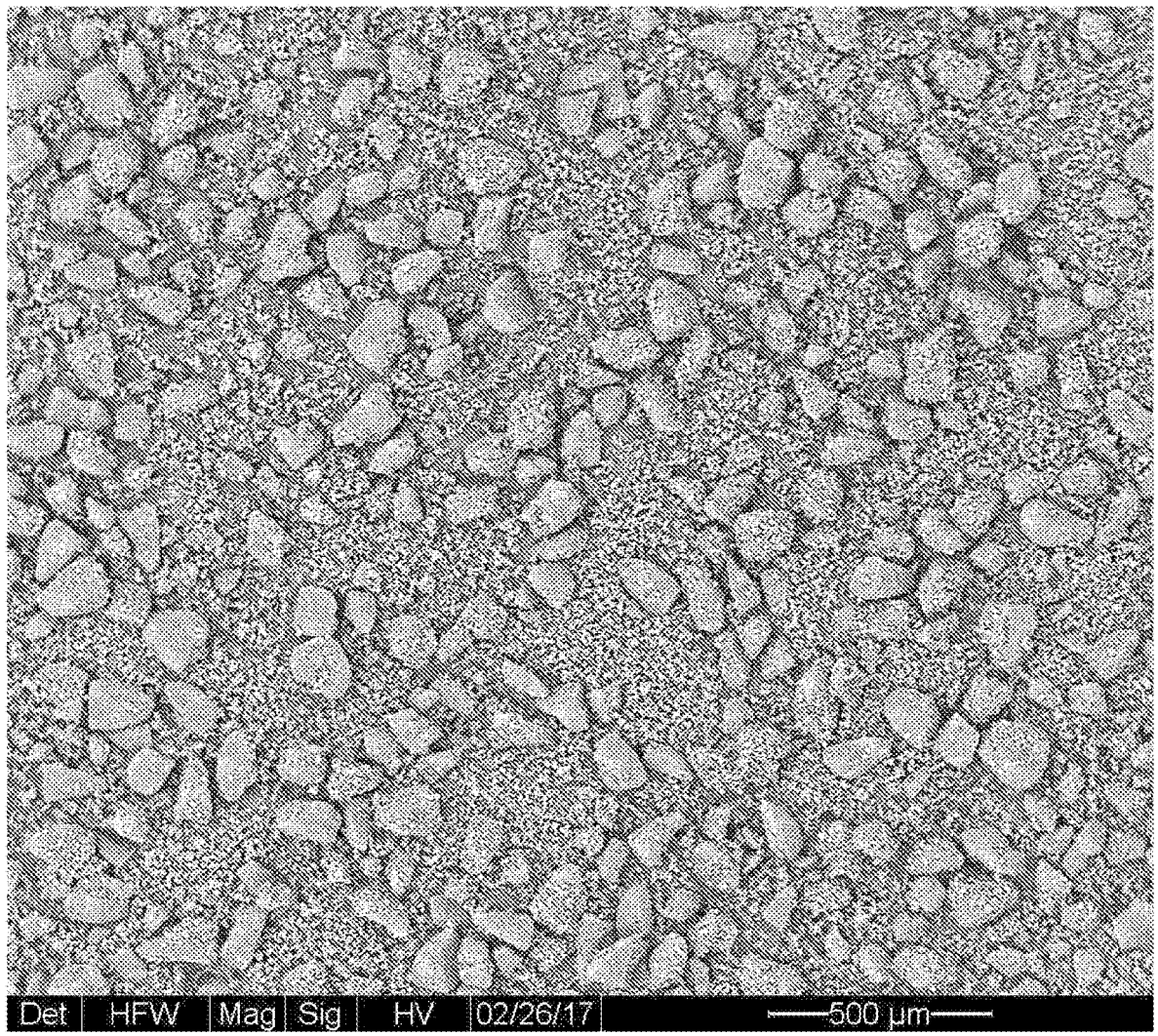
FIG. 7 shows the SEM image (×100) of the mixture of lactose monohydrate (large polyhedrons) and alprazolam in the dry powder composition of the embodiments for intranasal administration.

FIG. 7 shows the small polyhedron particles of alprazolam having the narrow size distribution of 5-40 μm, which are dispersed between the large polyhedron particles of lactose ranging from 50 μm to 200 μm. FIG. 8a shows an X-ray analysis of the obtained alprazolam polyhedron particles, where the large particles containing C and O atoms only must be lactose, and the small particles additionally containing Cl atoms must be alprazolam.

Example 14: Oxycodone Hydrochloride Composition with Lactose Monohydrate

Oxycodone hydrochloride (2.3 g) was dissolved in 9.9 g of ethanol under stirring at 300 rpm. An appropriate size magnetic bar was placed in the receiver and lactose monohydrate (2.3 g) was added there. The stirring rate was set at 150 rpm. The clear and homogeneous solution of the drug was spray-dried using the Büchi Mini Spray-Dryer with inlet air temperature of 90° C. and outlet temperature of 56° C., thereby obtaining the dry powder of the active agent, which was further blended in-situ with lactose monohydrate in the receiver. Stirring in the receiver was being maintained during the entire process. Concentration of oxycodone hydrochloride in the composition was about 41% w/w and concentration of oxycodone base was about 37% w/w.

Example 15: SEM Imaging of the Oxycodone Hydrochloride Composition

Figure 9:
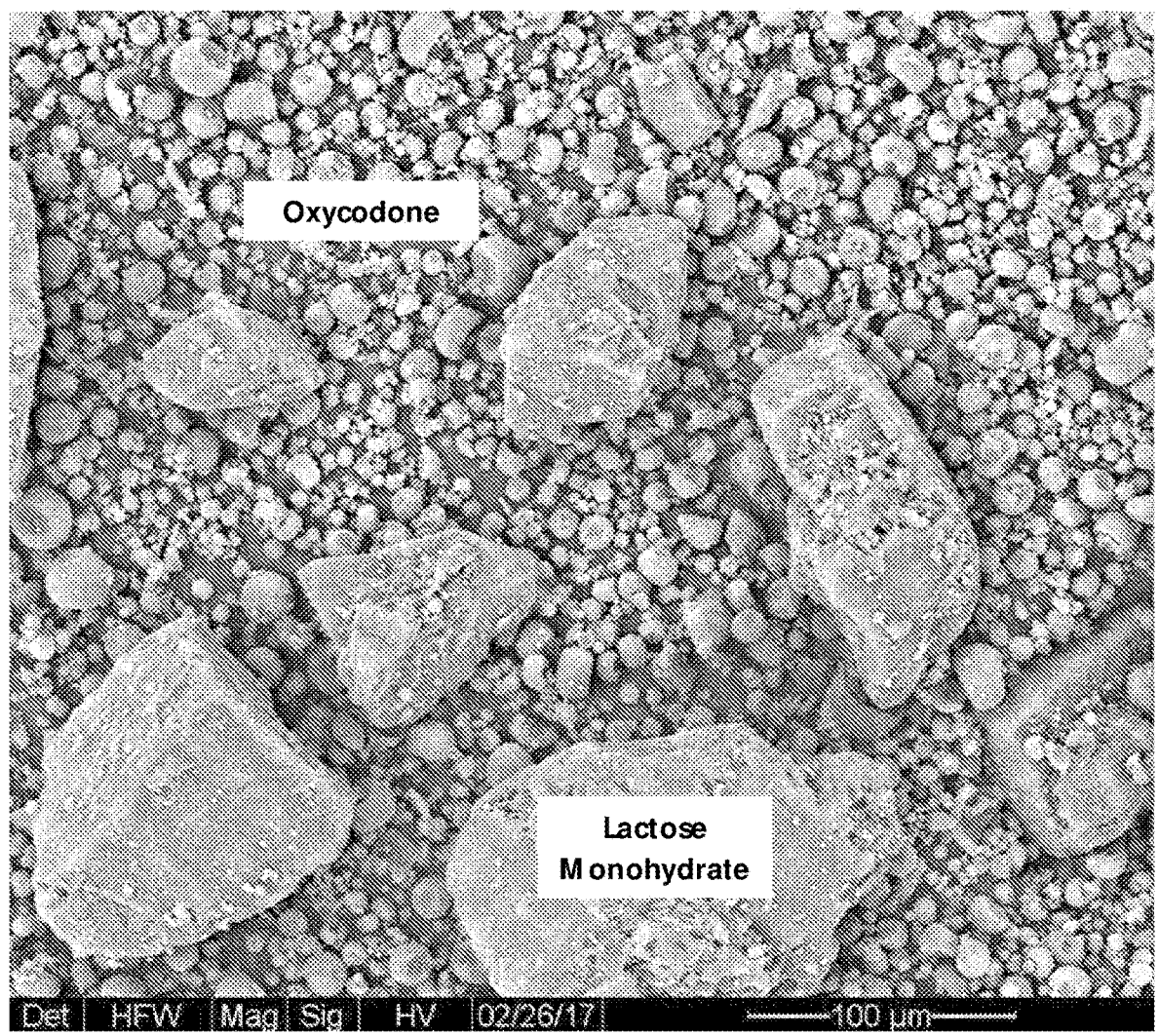
FIG. 9 shows the SEM images (×600) of the mixture of lactose monohydrate (large polyhedrons) and oxicodone hydrochloride (small non-aggregated spheres) in the dry powder composition of the embodiments for intranasal administration.

FIG. 9 shows the small spherical particles of oxycodone hydrochloride having the narrow size distribution of 3-30 μm, which are dispersed between the large polyhedron particles of lactose ranging from 50 μm to 200 μm.

Example 16: Particle Size Analysis of the Oxycodone Hydrochloride Composition

Figure 10:
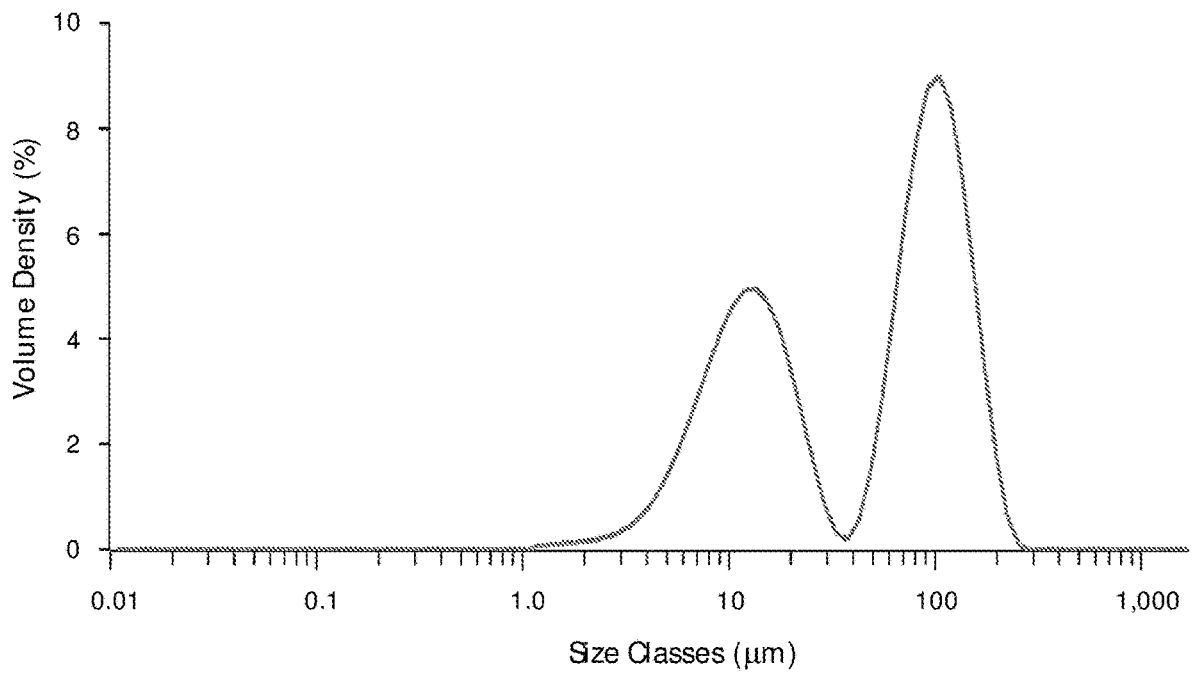
FIG. 10 shows the particle size distribution of the pharmaceutical composition of the embodiments (see Example 14). Two populations of particles is clearly seen: oxicodone hydrochloride in the range of 3-30 µm and lactose in the range of 50-200 µm. D(10)=57.4 am; D(50)=97.3 µm; D(90)=151 µm.

The oxycodone hydrochloride composition prepared in Example 14 was subjected to the particle size analysis using the Malvern Laser Diffraction instrument (see FIG. 10). The following particle size distribution was obtained: D(10)=7.7 μm, D(50)=64.4 μm and D(90)=141 μm. The amount of the particles having the size less than 5 μm was about 3% w/w.

Example 17: Dopamine Hydrochloride Composition with Lactose Monohydrate

Dopamine hydrochloride (2.3 g) was dissolved in a mixture of 7.0 g ethanol, 7.0 g acetone and 9.0 g water under stirring at 300 rpm. An appropriate size magnetic bar was placed in the receiver and lactose monohydrate (2.3 g) was added there. The stirring rate was set at 150 rpm. The obtained clear and homogeneous solution of the active agent was spray-dried using the Büchi Mini Spray-Dryer with inlet air temperature of 95° C. and outlet temperature of 65° C., thereby obtaining the dry powder of dopamine hydrochloride, which was further blended in-situ with lactose monohydrate in the receiver. Stirring in the receiver was being maintained during the entire process. Concentration of dopamine hydrochloride in the composition was about 37% w/w and concentration of dopamine base was about 26% w/w.

Example 18: Particle Size Analysis of the Dopamine Hydrochloride Composition The dopamine hydrochloride composition prepared in Example 17 was subjected to the particle size analysis using the Malvern Laser Diffraction instrument. The following particle size distribution was obtained: D(10)=8.0 μm, D(50)= 74.9 μm and D(90)=147 μm. The amount of the particles having the size less than 5 μm was about 3.5% w/w.

Example 19: Insulin Composition with Lactose Monohydrate 5 ml of insulin saline (sodium chloride) solution containing 500 IU of insulin was mixed with 7 ml of water under stirring at 300 rpm. An appropriate size magnetic bar was placed in the receiver and lactose monohydrate (2.3 g) was added there. The stirring rate was set at 150 rpm. The obtained clear and homogeneous solution of insulin was spray-dried using the Büchi Mini Spray-Dryer with inlet air temperature of 90° C. and outlet temperature of 56° C., thereby obtaining the insulin dry powder, which was further blended in-situ with lactose monohydrate in the receiver. Stirring in the receiver was being maintained during the entire process.

Example 20: SEM Imaging of the Insulin Composition

Figure 11:
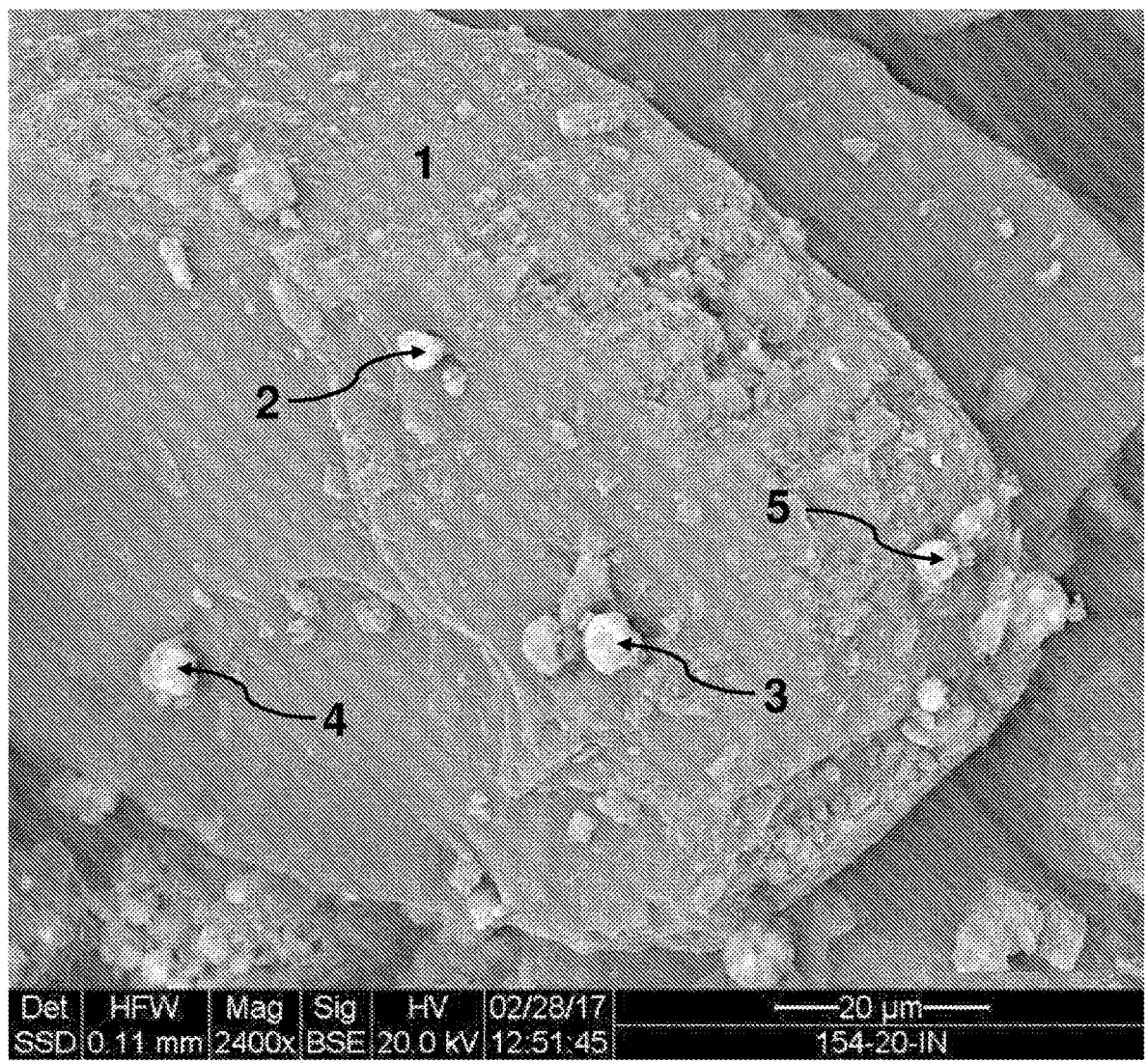
FIG. 11 shows the SEM image (×2400) of lactose monohydrate (large polyhedrons) (Particle 1) and insulin-sodium chloride (small spherical shape) (Particles 2, 3, 4 and 5) of the dry powder composition for intranasal administration.
Figure 12:
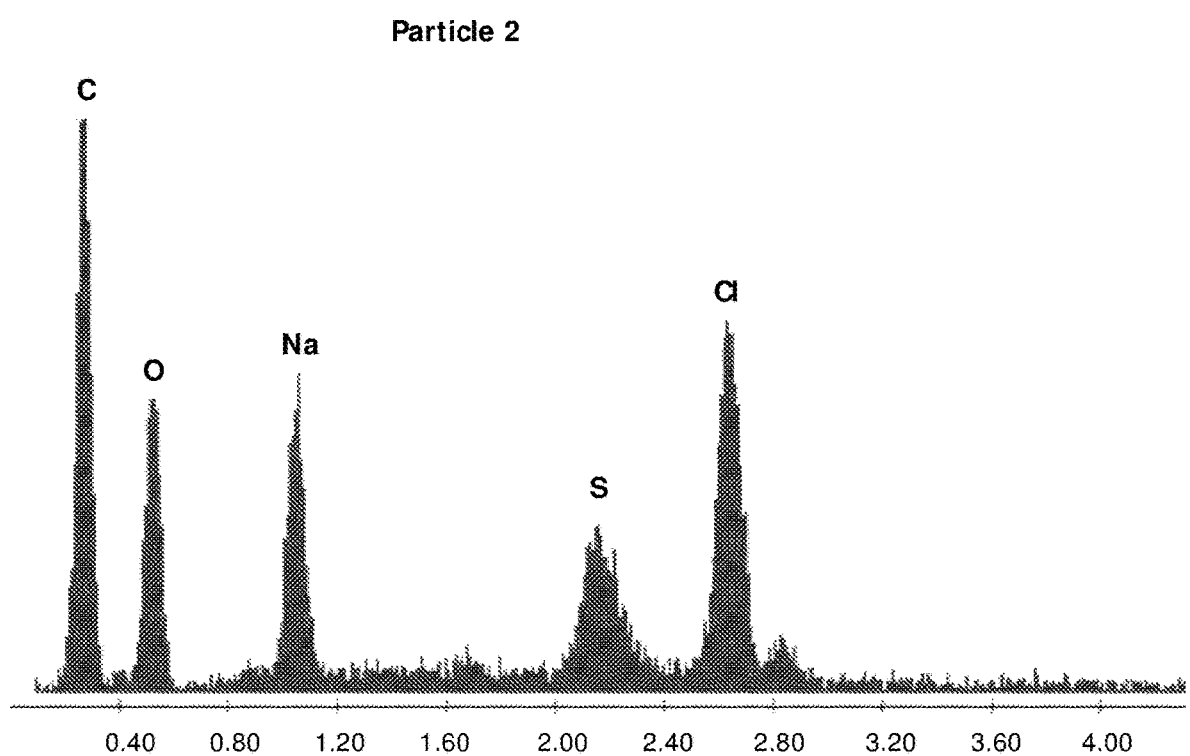
FIG. 12 shows the X-ray elemental analysis of Particle 2 containing "C", "O" and "S" atoms of insulin molecules and "Na" and "Cl" atoms of the sodium chloride salt.

FIG. 11 shows the small spherical particles of insulin-sodium chloride having the size of 5-7 μm laid on the surface of the large lactose polyhedron particles having the size above 100 μm. The elemental analysis shown on the FIG. 12 confirms that the particles include sodium chloride and sulphur, which is a clear indication that these particles are insulin.

Example 21: Particle Size Analysis of the Insulin Composition

Figure 13:
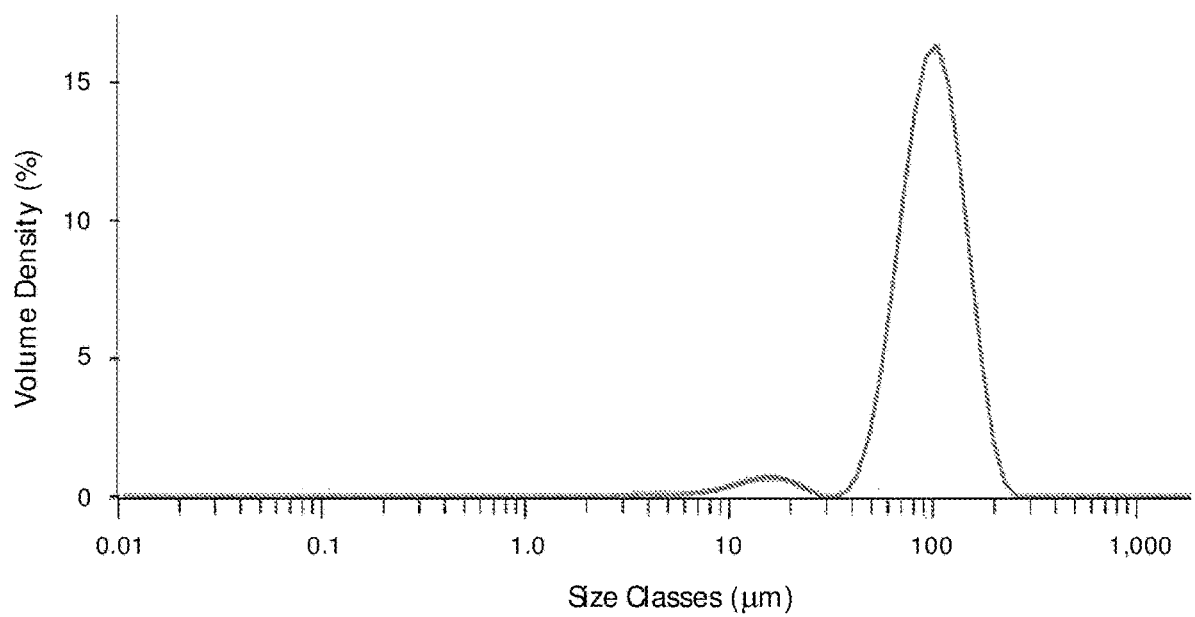
FIG. 13 shows the particle size distribution of the pharmaceutical composition of the embodiments (see Example 19). Two populations of the particles are clearly seen: insulin-sodium chloride particles in the range of 5-35 µm and lactose in the range of 50-200 µm. D(10)=57.4 µm; D(50)=97.3 µm; D(90)=151 µm.

The insulin composition prepared in Example 19 was subjected to the particle size analysis using the Malvern Laser Diffraction instrument. The following particle size distribution was obtained (see FIG. 13): D(10)=57.4 μm, D(50)=97.3 μm and D(90)=151 μm. The amount of the particles having the size less than 5 μm was about 0.3% w/w.

Example 22: Intranasal Drug Delivery

Aptar Unit-Dose Powder disposable devices were filled with the sumatriptan succinate composition prepared in Example 1. These devices were assembled according to the company guideline. Each device contained 10 mg of powder including 1 mg of sumatriptan succinate (100 mg/g as a labeled claim). Ten devices were packed, activated, and the powder delivered upon actuation of each device was collected and weighed. The weights (mg) of the delivered powder dose from the ten devices are shown in Table 1 below. Uniformity of the delivered dose (mg/g) from each of the ten devices, measured with an HPLC instrument according to the company protocol, is also shown in Table 1. In addition, Table 1 contains the data from the two devices that were stored for 6 months ("6M" in the table) at 40° C. and 75 RH.

TABLE 1

Delivered dose and uniformity of the delivered dose

| Sample name | Sample weight, mg | Sumatriptan base content, mg/g |
|---|---|---|
| Composition 1-1 | 10.04 | 103.40 |
| Composition 1-2 | 10.05 | 93.51 |
| Composition 1-3 | 10.07 | 108.63 |
| Composition 1-4 | 9.94 | 103.28 |
| Composition 1-5 | 10.07 | 91.54 |
| Composition 1-6 | 10.05 | 104.63 |
| Composition 1-7 | 10.04 | 99.15 |
| Composition 1-8 | 10.06 | 122.88 |
| Composition 1-9 | 10.03 | 109.75 |
| Composition 1-10 | 10.00 | 106.86 |
| AVG | 10.03 | 104.06 |
| RSD, % | 0.4 | 8.5 |
| Composition 1-11 (6 M) | 9.79 | 97.42 |
| Composition 1-12 (6 M) | 9.82 | 104.95 |
| AVG | 9.8 | 101.2 |
| RSD, % | 0.3 | 7.4 |

Example 23: Plume Geometry and Spray Pattern

Evaluation of the Plume Geometry and Spray Pattern of the compositions actuated from the Aptar Unit-Dose Powder (UDP) disposable devices was conducted using FDA's CMC Guidance (9). Three replicates of each composition either fresh prepared or stored were tested for: Plume angle (°); Plume width at 6 cm; Plume length (cm) and duration time (ms). Results from two spray-patterns (3 and 6 cm) were recorded providing details on diameter min (cm), diameter max (cm), area and ovality ratio. An appropriate high-resolution visualisation technique was used.

Example 24: PK Evaluation Following Single Intranasal or Oral Dose Administration of Oxycodone in Rats The objective of this study was to determine the pharmacokinetic profile of oxycodone following single administration of oral solution of oxycodone hydrochloride in PBS buffer and intranasal (IN) powder of oxycodone composition of invention described in the Example 14. The dosing was done at 10 mg/kg (2 mg per rat) by oral gavage or by modified intranasal Aptar device to 12 SD male rats for each rout of administration.

Study variables and end points were measured as following:
1) Morbidity and Mortality—daily.
2) Body weight—was measured during acclimation and before Test Item administrations.
3) Clinical sign observation—animals were observed for toxic signs after dosing.
4) Blood withdrawal—blood samples were collected at baseline (24 hours before dosing), 5, 15, 40, 60, 90, 120, 240 and 420 minutes after administration (three rats per bleeding time points for each Rout of administration).
5) Brains were removed after bleeding at time points: 15, 60, 120 and 420 minutes (three rats at each time point for each Rout of administration)

$T_{max}$, $C_{max}$ and $AUC_t$ (area under the concentration-time curve from zero up to a definite time t, the parameter that is used as an index of the drug exposure of the body, when referred to the plasma drug levels, and is closely dependent on the drug amount that enter into the systemic circulation).

The brain PK parameters were measured in the similar manner and reported as drug concentration in the ml of homogenized brain tissues. These samples were analysed for oxycodone content by a HPLC-UV method. The obtained plasma pharmacokinetic parameters of the oral and the intranasal products are shown in Table 2 and FIG. 14.

TABLE 2

Oxycodone pharmacokinetic parameters in rat's plasma

| Oxycodone Product | $AUC_{0-420}$ (µg*min/ml) | $T_{max}$ (min) | $C_{max}$ (µg/ml) | $C_{max\,IN}/C_{max\,ORAL}$ (%) | $AUC_{IN}/AUC_{ORAL}$ (%) |
|---|---|---|---|---|---|
| Intranasal powder | 4.23 | 5 | 1.88 | 2.98 | 1.49 |
| Oral gavage | 2.83 | 60 | 0.63 | | |

As can be seen from the Table 2 and FIG. 14, the $C_{max}$ value is almost 3 folds higher, while the AUS value is increased at 1.5 folds upon intranasal administration. The comparative value of $T_{max}$ of 5 min versus 60 min demonstrates the extremely fast onset of action following intranasal administration of oxycodone. The very fast nasal transmucosal absorption is manifested by the immediate increase in plasma oxycodone concentration, since it is observed following the administering of only the intranasal powder. The initial increase is later followed by the second peak of 60 min, exhibiting the gastrointestinal absorption, which is seen both in the intranasal and oral oxycodone formulations.

As the intranasal formulation has been reported to have a more rapid onset of effect (10, 11), which is attributed to the rapid increase in blood levels, the present results suggest that oxycodone intranasal powder also has a fast pain relief onset of action.

The obtained brain pharmacokinetic parameters of the oral and the intranasal products are shown in Table 3 and FIG. 15.

TABLE 3

Oxycodone pharmacokinetic parameters in rat's brains

| Oxycodone Product | $AUC_{0-420}$ (µg*min/ml) | $T_{max}$ (min) | $C_{max}$ (µg/ml) | $C_{max\,IN}/C_{max\,ORAL}$ (%) | $AUC_{IN}/AUC_{ORAL}$ (%) |
|---|---|---|---|---|---|
| Intranasal powder | 29.03 | 420 | 6.63 | 12.05 | 11.52 |
| Oral gavage | 2.52 | 120 | 0.55 | | |

As can be seen from the Table 3 and FIG. 15, the $C_{max}$ value is 12 folds higher, while the AUS value is increased 11.5 times upon intranasal administration. The $T_{max}$ value of 420 min versus 120 min demonstrates the sustained action of oxycodone following intranasal administration. However, the concentrations of the drug after 15 min were found to be 2.94 µg/ml and 0.23 µg/ml for intranasal and oral route, respectively. This is the clear evidence that the immediate and huge increase of oxycodone concentration in brain is a result of the direct drug delivery to the brain via intranasal route exclusively. The oxycodone peak in brain of 120 min following the gastrointestinal absorption is typical for oral oxycodone formulations.

The rapid onset and prolonged action of oxycodone demonstrated in the present application is a significant breakthrough in the post-surgery pain management of patients. Both oral and intranasal formulations were well tolerated. No toxic signals or any abnormal effects were observed.

Intranasal Naloxone Formulations

Materials

Naloxone hydrochloride (Noramco); lactose monohydrate (Meggle Pharma); ethanol (BioLab).

Methods

The spray-drying process was carried out using the Mini Spray Dryer B-290 of Büchi Labortechnik AG. A magnetic stirrer (Fried Electric) was placed under the receiver (receiving chamber), a magnetic bar of appropriate size was inserted into the receiver, and then the diluent was added. The liquid feed containing at least one active agent was prepared by dissolving at least one active compound in the selected solvent or mixture of solvents. Quantification was performed using HPLC and a Dionex HPLC instrument. A FEI Quanta-200 Scanning Electron Microscope (SEM) equipped with an Everhart-Thornley Detector was used to obtain the images of the spray-dried powder. The accelerating voltage of 20 kV was applied to provide magnification from 250 to 10,000 times. In addition, an X-ray Element Analysis Detector (Link ISIS, Oxford Instruments, England) was used to determine the drug and particle identity and their distribution throughout DPI. Particle size was measured using the Malvern Mastersizer 3000 series based on the Light Diffraction method.

Naloxone assay in the compositions was determined using Dionex HPLC-PDA instrument equipped with Chromeleon software; Column & packing: LiChroCart®125-4, Li Chrospher®60 RP-select B, 5p, Part. No. 1.50213.0001.

Mobile Phase: A: Acetonitrile: Tetrahydrofuran: Solution A(20:40:940 v/v/v)

B: Acetonitrile: Tetrahydrofuran: Solution A(170:40:790 v/v/v)

Gradient Program:

| Time (min) | Mobile Phase A (%) | Mobile Phase B (%) |
|---|---|---|
| 0 | 100 | 0 |
| 40 | 0 | 100 |
| 50 | 0 | 100 |
| 50.5 | 100 | 0 |
| 60 | 100 | 0 |

Flow rate: 1.5 ml/min
Injection volume: 20 µL
Detector: UV, 230 nm
Column temperature: 40° C.
Auto sampler temperature: ambient
Run time: 60 min
Diluent: 0.1M Hydrochloric acid
RT of Naloxone peak: about 11 min Example 25: Modification of the Commercial Büchi Labortechnik AG Spray-Dryer FIG. 2 schematically shows a modified spray dryer of the embodiments. A Mini Spray-Dryer B-290 of Büchi Labortechnik AG was modified by:

1. Addition of a magnetic bar into the glass receiver and placing a magnetic stirrer under the continuously rotating glass receiver of the spray-dryer.
2. Selection of a suitable two-fluids spraying nozzle for spraying the solution containing only an active agent (without diluent) into fine droplets suitable for the preparation of 10-30 µm dry powder particles of the active agent. One of the fluids is the clear and homogeneous solution of the active agent, and the second fluid is the drying gas.

Example 26: Naloxone Hydrochloride Composition with Lactose Monohydrate

Naloxone hydrochloride (3.0 g) was dissolved for 20 min in 24 g of ethanol-water mixture (50:50) under stirring at 300 rpm. An appropriate size magnetic bar was placed in the receiver and lactose monohydrate (3.0 g) was added there. The stirring rate was set at 150 rpm. The obtained clear and homogeneous solution of the drug was spray-dried using the Büchi Mini Spray-Dryer with inlet air temperature of 115° C. and outlet temperature of 90° C., thereby obtaining the dry powder of naloxone hydrochloride, which was further blended in-situ with lactose monohydrate in the receiver. The stirring was being maintained in the receiver during the entire process. The loading of naloxone hydrochloride into the composition was about 26% w/w. The obtained composition was then mixed with an additional amount of lactose in order to reach the 20% API loading.

Example 27: SEM Imaging of the Naloxone Hydrochloride Composition

The SEM images (FIG. 16) show that the small spherical particles of naloxone hydrochloride having the narrow size distribution of 5-30 μm are dispersed between large shapeless particles of lactose ranging between 40 μm to 240 μm.

Example 28: Particle Size Analysis of the Naloxone Hydrochloride Composition The naloxone hydrochloride composition prepared in Example 26 was subjected to the particle size analysis using the Malvern Laser Diffraction instrument. The following particle size distribution was obtained: D (10)=10.5 μm, D (50)=77.7 μm and D (90)=144 μm. The amount of the obtained particles having the size less than 10 μm was about 9.5% v/v. 5 μm was about 4.9% v/v.

Conclusions:
Particle size distribution of Naloxone Microspheres powder Bulk Drug Product specification and safety requirements

Example 29: Naloxone HCl Drug-Device Combination Product Preparation

Aptar Unit-Dose Powder disposable devices were filled with the naloxone HCl composition prepared in Example 26. These devices were assembled according to the company guideline. Each device contained 20 mg of powder including 4 mg of naloxone hydrochloride (200 mg/g as a labeled claim).

Example 30: Naloxone HCl Drug-Device Combination Product Net Fill Weight and Delivered Dose Uniformity tests Ten devices were packed, activated, and the powder delivered upon actuation of each device (shot weight) was collected and weighed. The weights (mg) of the delivered powder dose from the ten devices are shown in Table 4 below. Uniformity of the delivered dose (mg/device and %) from each of the ten devices, measured with an HPLC instrument according to the company protocol, is also shown in Table 4.

TABLE 4

| | Net fill weight and uniformity of delivered doses | | |
|---|---|---|---|
| Sample name | Sample (shot) weight, mg | Naloxone content, mg/device | Naloxone content, %/device |
| Device 1 | 19.04 | 3.77 | 99.05 |
| Device 2 | 19.42 | 3.84 | 98.76 |
| Device 3 | 19.05 | 3.77 | 98.85 |
| Device 4 | 19.26 | 3.76 | 97.74 |
| Device 5 | 19.96 | 3.89 | 97.39 |
| Device 6 | 19.94 | 3.90 | 97.75 |
| Device 7 | 20.16 | 3.74 | 92.85 |
| Device 8 | 19.34 | 3.66 | 94.61 |
| Device 9 | 18.82 | 3.65 | 97.10 |
| Device 10 | 20.07 | 3.82 | 95.10 |
| AVG | 19.51 | 3.78 | 96.92 |
| RSD, % | 2.49 | 2.20 | 2.13 |

Conclusions:
i. Net fill weight of Naloxone Intranasal Product comply Combination (Drug-Device) Product Specification and USP <755> requirements
ii. Delivered Dose Uniformity (10 units) of Naloxone Intranasal Product comply Combination (Drug-Device) Product Specification and USP <601> requirements

Example 31: Stability Data of Naloxone Drug-Device Combination Product in Accelerating Aging Conditions The naloxone hydrochloride combination products prepared in Example 29 was subjected to accelerating aging conditions at 40° C.±2° C./75% RH±5% RH. The six months stability data is presented in Table 5.

TABLE 5

| | Stability data | | | |
|---|---|---|---|---|
| | Tests and Specifications | | | |
| Testing interval, month | Appearance | Assay (HPLC) | Impurities/ Degradation Product | Water Content |
| Specifications | Disposable plastic device, white color, no visible damages | 4.0 ± 0.4 mg in device (90.0-110.0%) | A. ≤0.5% B. ≤0.5% C. ≤0.5% F. ≤0.5% E. ≤0.5% Unspecified impurities: ≤0.5% | NMT 7.0% |

TABLE 5-continued

Stability data

| | Tests and Specifications | | | |
|---|---|---|---|---|
| Testing interval, month | Appearance | Assay (HPLC) | Impurities/ Degradation Product | Water Content |
| Initial | Disposable plastic device, white color, no visible damages | Assay of Naloxone hydrochloride 4.1 mg in device (103.4%) Assay of Naloxone 3.8 mg in device (94.3%) | for each Total Impurities: ≤4.0% A. ≤BRL [1] B. ≤BRL C. ≤BRL F. ≤BRL E. ≤BRL Unspecified impurities: ND[2] Total Impurities: ≤BRL | 6.2% |
| 6 | Disposable plastic device, white color, no visible damages | Assay of Naloxone hydrochloride 4.1 mg in device (103.4%) Assay of Naloxone 3.8 mg in device (94.3%) | A. 0.1% B. ≤BRL C. 0.2% F. ≤BRL E. ≤BRL D. ≤BRL Unspecified impurities: Imp (RRT1.35) 0.3% Imp (RRT1.9) 0.2% Total Impurities: 0.8% | 1.7% |

[1] below reporting limit (0.05%)
[2] Not Detected

Conclusions: Powdered naloxone formulation according to the present invention showed good stability after 6 months at 40° C. and 75% Related Humidity RH. It contained 0.8% of the total impurities and similar assay of API. All results meet drug device combination products stability specifications.

Example 32 Structural Characterisation of Naloxone Microspheres Powder

Phase analysis of two naloxone samples was performed by the X-ray powder diffraction (XRPD) method. The data were collected on a Panalytical Empyrean powder diffractometer (Cu Kα radiation, λ=1.54178 Å) equipped with an X'Celerator linear detector and operated at V=40 kV, I=30 mA. Scans were run in a 2q range of 3-38° with step equal to ~0.0167°, scan speed ~0.042°/sec. Peak lists were automatically generated using Match! 2 p-XRD analysis software.

XRD pattern images of raw naloxone HCl, lactose monohydrate and microspheres mixed with lactose monohydrate batch PNLX070729 of the present invention are shown in FIG. 18.

As can be seen from FIG. 18, no naloxone HCl peaks are observed in the pattern of naloxone microspheres. The determined peaks belong to lactose monohydrate, only suggesting that naloxone HCl has an amorphous structure.

Remarkably, this amorphous structure was shown to be stable for 6 months, as shown in FIG. 19. The bottom pattern belongs to the initial product while the upper curve reflects the structure after six months. Both patterns are similar.

Thus not only is naloxone stable for at least 6 months, it also retains an amorphous structure.

Example 33: Comparative Pharmacokinetic Study Between Microspheres Nasal Powder 4 mg for and NARCAN® Nasal Spray 4 mg Study NP-001 was a Phase 1, open-label, single-dose, randomized 2-period, 2-treatment, 2-sequence, crossover study. The primary objective of this study was to compare the bioavailability (BA) of naloxone between FMXIN001 naloxone formulation according to the present invention (Microspheres Nasal Powder 4 mg) and NARCAN® (Nasal Spray 4 mg) after administration of a single dose in healthy subjects under fasted conditions. The secondary objective of this study was to evaluate the safety and tolerability of the study treatments.

PK blood samples were collected prior to dosing (0-hour) and at 0.017, 0.033, 0.05, 0.067, 0.1, 0.133, 0.167, 0.25, 0.333, 0.417, 0.5, 0.75, 1, 2, 3, 4, 6, and 8 hours after drug administration, for a total of 19 samples in each period. The 2 study periods were separated by a washout of 4 days, corresponding to more than 5 times the expected half-life ($t_{1/2}$) of naloxone to prevent any possible carry-over effect. The PK parameters maximum plasma concentration ($C_{max}$), area under the drug concentration versus time curve from time 0 to the time of last measurable analyte concentration ($AUC_t$), area under the drug concentration versus curve from time 0 to infinity ($AUC_{inf}$), area under the drug concentration versus time curve from time 0 to 4 minutes ($AUC_{0-4\ min}$), area under the drug concentration versus time curve from time 0 to 10 minutes ($AUC_{0-10\ min}$), area under the drug concentration versus time curve from time 10 to 30 minutes ($AUC_{10-30\ min}$), time to maximum plasma concentration ($T_{max}$), apparent first-order elimination rate constant ($K_{el}$), and elimination half-life ($t_{1/2}$) were estimated using a noncompartmental approach for total naloxone and unconjugated naloxone (naloxone is metabolized in the liver, primarily by glucuronide conjugation with naloxone-3-glucoronide as the major metabolite).

Study Results

Subject Disposition

Study NP-001 included a total of 14 healthy subjects (6 males and 8 females) with a mean age of 43 years (range, 26-58 years). All 14 subjects received both treatments (FMXIN001 Microspheres Nasal Powder 4 mg and NARCAN® Nasal Spray 4 mg) and completed the study.

Comparative Bioavailability and Bioequivalence

For total naloxone, the total systemic exposure, as measured by $AUC_t$ and $AUC_{inf}$, were relatively similar ($AUC_t$ ratio=104.31%; $AUC_{inf}$ ratio=102.65%) for FMXIN001 Microspheres Nasal Powder 4 mg compared to NARCAN® Nasal Spray 4 mg. The peak systemic exposure, as measured by $C_{max}$, was approximately 1.1-fold greater for FMXIN001 Microspheres Nasal Powder 4 mg compared to NARCAN® Nasal Spray 4 mg.

Partial exposure as measured by $AUC_{0-4\ min}$, $AUC_{0-10\ min}$, and $AUC_{10-30\ min}$, was approximately 7-fold, 4-fold, and 1.5-fold greater, respectively, for FMXIN001 Microspheres Nasal Powder 4 mg compared to NARCAN® Nasal Spray 4 mg.

The median $T_{max}$ occurred approximately 30 minutes earlier for FMXIN001 Microspheres Nasal Powder 4 mg as compared to NARCAN® Nasal Spray 4 mg. The results of the nonparametric analysis show that there was no statistically significant difference in $T_{max}$ (p=0.2080) between treatments. A significant treatment effect was detected by ANOVA in the analysis of $AUC_{0-4\ min}$ (p<0.0001), $AUC_{0-10\ min}$ (p=0.0002), and $AUC_{10-30\ min}$ (p=0.0088).

A summary of all mean PK parameters for total naloxone is provided in Table 6 and the concentration-time profile is provided in FIG. 20.

TABLE 6

Mean Pharmacokinetic Parameters for Plasma Total Naloxone

| Mean Parameters (CV %) | Treatment N = 14 | |
| --- | --- | --- |
| | FMXIN001 Microspheres Powder 4 mg | NARCAN® Nasal Spray 4 mg |
| $C_{max}$ (ng/mL) | 36.74 (30) | 33.83 (44) |
| $T_{max}^a$ (h) | 1.0 (0.25-2.05) | 1.50 (0.42-2.0) |
| $AUC_t$ (ng · h/mL) | 98.06 (15) | 94.52 (19) |
| $AUC_{inf}$ (ng · h/mL) | 108.89 (20) | 103.61 (21) |
| $AUC_{0-4\ min}$ (ng · h/mL) | 0.14 (88) | 0.02 (111) |
| $AUC_{0-10\ min}$ (ng · h/mL) | 1.30 (69) | 0.39 (63) |
| $AUC_{10-30\ min}$ (ng · h/mL) | 7.51 (33) | 5.14 (53) |
| $t_{1/2}$ (h) | 2.53 (58) | 2.28 (23) |
| $K_{el}$ (1/h) | 0.33 (35) | 0.32 (22) |

$AUC_{0-4\ min}$ = area under the drug concentration versus time curve from time 0 to 4 minutes;
$AUC_{0-10\ min}$ = area under the drug concentration versus time curve from time 0 to 10 minutes;
$AUC_{10-30\ min}$ = area under the drug concentration versus time curve from time 10 to 30 minutes;
$AUC_{inf}$ = area under the drug concentration versus time curve from time 0 to infinity;
$AUC_t$ = area under the drug concentration versus time curve from time 0 to the time of the last measurable analyte concentration;
$C_{max}$ = maximum plasma concentration;
CV = coefficient of variation;
$K_{el}$ = first order elimination rate constant;
$t_{1/2}$ = elimination half-life
$T_{max}$ = time to maximum plasma concentration
$^a$Median (range) is presented For unconjugated naloxone, the total systemic exposure, as measured by $AUC_t$ and $AUC_{inf}$ was approximately 1.26-fold greater for FMXIN001 Microspheres Powder 4 mg compared to NARCAN® Nasal Spray 4 mg. The peak systemic exposure, as measured by $C_{max}$, was approximately 1.6-fold greater for FMXIN001 Microspheres Nasal Powder 4 mg compared to NARCAN® Nasal Spray 4 mg.

Partial exposure as measured by $AUC_{0-4\ min}$, $AUC_{0-10\ min}$, and $AUC_{10-30\ min}$, was approximately 7-fold, 4-fold, and 1.6-fold greater, respectively, for FMXIN001 Microspheres Nasal Powder 4 mg compared to NARCAN® Nasal Spray 4 mg.

The median $T_{max}$ occurred approximately 5 minutes earlier for FMXIN001 Microspheres Nasal Powder 4 mg as compared to NARCAN® Nasal Spray 4 mg. The results of the nonparametric analysis show that there was no statistically significant difference in $T_{max}$ (p=0.1387) between treatments. A significant treatment effect was detected by ANOVA in the analysis of $AUC_t$ (p=0.0182), $AUC_{inf}$ (p=0.0190), $C_{max}$ (p=0.0001), $AUC_{0-4\ min}$ (p<0.0001), $AUC_{0-10\ min}$ (p<0.0001), and $AUC_{10-30\ min}$ (p=0.0001).

A summary of all mean PK parameters for unconjugated naloxone is provided in Table 7 and the concentration-time profile is provided in FIG. 21.

TABLE 7

Mean Pharmacokinetic Parameters for Plasma Unconjugated Naloxone

| Mean Parameters (CV %) | Treatment N = 14 | |
| --- | --- | --- |
| | FMXIN001 Microspheres Powder 4 mg | NARCAN® Nasal Spray 4 mg |
| $C_{max}$ (ng/mL) | 11.80 (42) | 7.06 (32) |
| $T_{max}^a$ (h) | 0.25 (0.13-0.75) | 0.33 (0.17-0.75) |
| $AUC_t$ (ng · h/mL) | 14.35 (25) | 11.63 (33) |
| $AUC_{inf}$ (ng · h/mL) | 14.53 (25) | 11.81 (33) |
| $AUC_{0-4\ min}$ (ng · h/mL) | 0.12 (86) | 0.02 (100) |
| $AUC_{0-10\ min}$ (ng · h/mL) | 0.94 (69) | 0.29 (65) |
| $AUC_{10-30\ min}$ (ng · h/mL) | 3.01 (34) | 1.87 (40) |
| $t_{1/2}$ (h) | 1.29 (14) | 1.29 (12) |
| $K_{el}$ (1/h) | 0.55 (13) | 0.54 (11) |

$AUC_{0-4\ min}$ = area under the drug concentration versus time curve from time 0 to 4 minutes;
$AUC_{0-10\ min}$ = area under the drug concentration versus time curve from time 0 to 10 minutes;
$AUC_{10-30\ min}$ = area under the drug concentration versus time curve from time 10 to 30 minutes;
$AUC_{inf}$ = area under the drug concentration versus time curve from time 0 to infinity;
$AUC_t$ = area under the drug concentration versus time curve from time 0 to the time of the last measurable analyte concentration;
$C_{max}$ = maximum plasma concentration;
CV = coefficient of variation;
$K_{el}$ = first order elimination rate constant;
$t_{1/2}$ = elimination half-life
$T_{max}$ = time to maximum plasma concentration
$^a$Median (range) is presented A statistical summary for the least square (LS) means, ratio of means, and confidence intervals (CIs) for FMXIN001 Microspheres Nasal Powder 4 mg versus NARCAN® Nasal Spray 4 mg for total naloxone and unconjugated naloxone are presented in Table 8 and Table 9, respectively.

TABLE 8

LS Geometric Means, Ratio of Means, and 90% CIs for FMXIN001 Microspheres Powder 4 mg versus NARCAN ® Nasal Spray 4 mg for Total Naloxone

| Parameters | LS Geometric Mean N = 14 | | Ratio (%) | 90% CI |
|---|---|---|---|---|
| | FMXIN001 Microspheres Powder 4 mg | NARCAN ® Nasal Spray 4 mg | | |
| $C_{max}$ (ng/mL) | 35.27 | 31.61 | 111.58 | 91.29-136.39 |
| $AUC_t$ (ng · h/mL) | 96.97 | 92.96 | 104.31 | 99.39-109.47 |
| $AUC_{inf}^a$ (ng · h/mL) | 107.0 | 104.24 | 102.65 | 97.54-108.02 |
| $AUC_{0-4\ min}$ (ng · h/mL) | 0.07 | 0.010 | 696.13 | 525.43-922.27 |
| $AUC_{0-10\ min}$ (ng · h/mL) | 1.04 | 0.25 | 410.95 | 249.62-676.56 |
| $AUC_{10-30\ min}$ (ng · h/mL) | 7.14 | 4.62 | 154.67 | 120.59-198.38 |

$AUC_{0-4\ min}$ = area under the drug concentration versus time curve from time 0 to 4 minutes;
$AUC_{0-10\ min}$ = area under the drug concentration versus time curve from time 0 to 10 minutes;
$AUC_{10-30\ min}$ = area under the drug concentration versus time curve from time 10 to 30 minutes;
$AUC_{inf}$ = area under the drug concentration versus time curve from time 0 to infinity;
$AUC_t$ = area under the drug concentration versus time curve from time 0 to the time of the last measurable analyte concentration;
CI = confidence interval;
$C_{max}$ = maximum plasma concentration;
LS = least squares
$^a$N = 13 for FMXIN001 Microspheres Powder 4 mg and N = 12 for NARCAN ® Nasal Spray due to analytical reasoning

TABLE 9

LS Geometric Means, Ratio of Means, and 90% CIs for FMXIN001 Microspheres Powder 4 mg versus NARCAN ® Nasal Spray 4 mg for Unconjugated Naloxone

| Parameters | LS Geometric Mean N = 14 | | Ratio (%) | 90% CI |
|---|---|---|---|---|
| | FMXIN001 Microspheres Powder 4 mg | NARCAN ® Nasal Spray 4 mg | | |
| $C_{max}$ (ng/mL) | 10.95 | 6.75 | 162.29 | 138.29-190.45 |
| $AUC_t$ (ng · h/mL) | 13.94 | 11.04 | 126.32 | 108.46-147.12 |
| $AUC_{inf}$ (ng · h/mL) | 14.11 | 11.21 | 125.87 | 108.18-146.46 |
| $AUC_{0-4\ min}$ (ng · h/mL) | 0.07 | 0.01 | 683.48 | 447.84-1043.1 |
| $AUC_{0-10\ min}$ (ng · h/mL) | 0.74 | 0.20 | 373.24 | 253.04-550.53 |
| $AUC_{10-30\ min}$ (ng · h/mL) | 2.86 | 1.74 | 164.27 | 138.93-194.24 |

$AUC_{0-4\ min}$ = area under the drug concentration versus time curve from time 0 to 4 minutes;
$AUC_{0-10\ min}$ = area under the drug concentration versus time curve from time 0 to 10 minutes;
$AUC_{10-30\ min}$ = area under the drug concentration versus time curve from time 10 to 30 minutes;
$AUC_{inf}$ = area under the drug concentration versus time curve from time 0 to infinity;
$AUC_t$ = area under the drug concentration versus time curve from time 0 to the time of the last measurable analyte concentration;
CI = confidence interval;
$C_{max}$ = maximum plasma concentration;
LS = least squares Overall, FMXIN001 Microspheres Nasal Powder 4 mg displayed greater peak and total systemic exposure, with earlier onset of action (supported by greater partial exposures) for total and unconjugated naloxone when compared to NARCAN® Nasal Spray 4 mg after a single dose in healthy subjects under fasted conditions.

These results demonstrate that the FMXIN001 Microspheres Nasal Powder drug delivery system (UDS) results in exposures that are either comparable or superior to NARCAN® Nasal Spray.

Safety

The administration of FMXIN001 Microspheres Nasal Powder 4 mg was generally well tolerated by the healthy subjects who participated in this study.

A total of 9 treatment-emergent adverse events (TEAEs) affecting 4 subjects (28.6% of subjects dosed) were reported during administration of FMXIN001 Microspheres Nasal Powder and NARCAN® Nasal Spray. All TEAEs were considered mild in severity, possibly related to the study treatment, not related to the study device, and resolved prior to the end-of-study without intervention. The most prevalent TEAE was bradycardia, with 3 events affecting 2 subjects (14.3%) (Table 7).

No subject discontinued from the study due to a TEAE, and none of the TEAEs required the use of concomitant therapy. No serious adverse events (SAEs) were reported during the conduct of the study and none of the AEs had a significant impact on the safety of the subjects or on the integrity of the study results.

Overall, the safety profile of FMXIN001 Microspheres Nasal Powder was comparable to the safety profile of NARCAN® Nasal Spray (Table 10).

TABLE 10

Summary of Adverse Events

| System Organ Class Preferred Term | Incidence by Treatment Group n(%) of Subjects | | |
|---|---|---|---|
| | FMXIN001 Microspheres Powder 4 mg N = 14 | NARCAN ® Nasal Spray 4 mg N = 14 | Total N = 14 |
| Subjects with 1 or More TEAEs | 3 (21.4%) | 3 (21.4%) | 4 (28.6%) |
| Subjects with No TEAEs | 11 (78.6%) | 11 (78.6%) | 10 (71.4%) |
| Cardiac Disorders | 1 (7.1%) | 2 (14.3%) | 2 (14.3%) |
| Bradycardia | 1 (7.1%) | 2 (14.3%) | 2 (14.3%) |
| Investigations | 1 (7.1%) | 2 (14.3%) | 2 (14.3%) |
| Electrocardiogram PR Prolongation | 0 (0%) | 1 (7.1%) | 1 (7.1%) |
| Electrocardiogram QT Prolongation | 1 (7.1%) | 1 (7.1%) | 1 (7.1%) |
| Nervous System Disorders | 1 (7.1%) | 0 (0%) | 1 (7.1%) |
| Dizziness | 1 (7.1%) | 0 (0%) | 1 (7.1%) |
| Respiratory, Thoracic, and Mediastinal Disorders | 1 (7.1%) | 0 (0%) | 1 (7.1%) |
| Tachypnoea | 1 (7.1%) | 0 (0%) | 1 (7.1%) |
| Skin and Subcutaneous Tissue Disorders | 1 (7.1%) | 0 (0%) | 1 (7.1%) |
| Cold Sweat | 1 (7.1%) | 0 (0%) | 1 (7.1%) |

TEAE = treatment-emergent adverse event

Dose Accuracy

To evaluate the dose accuracy of FMXIN001 Microspheres Nasal Powder compared to NARCAN® Nasal Spray after device actuation, the weight of each study drug device was measured and documented within 2 hours before the first subject dosing time and after the last subject's drug administration. The device weight differences for each subject administered FMXIN001 Microspheres Nasal Powder and NARCAN® Nasal Spray are provided in Table 11 and Table 12, respectively.

Overall, the dose accuracy was comparable between FMXIN001 Microspheres Nasal Powder and NARCAN® Nasal Spray. The average dose remaining in each device after actuation of the drug product was 0.018714 g (standard deviation [SD], 0.001485; relative standard deviation [RSD], 7.933057%) for FMXIN001 Microspheres Nasal Powder compared to 0.104214 g (SD, 0.003004; RSD, 2.882761%) for NARCAN® Nasal Spray. The dose accuracy of FMXIN001 Microspheres Nasal Powder was observed following pilot production and manual filling of devices. Automated commercial batches filling equipment can provide for uniform accuracy.

TABLE 11

Individual Dose Accuracy of FMXIN001 Microspheres Nasal Powder

| Subject | Period | Device Weight Before Dosing (g) | Device Weight After Dosing (g) | Device Weight Difference (g) |
|---|---|---|---|---|
| 1 | 2 | 6.601 | 6.583 | 0.018 |
| 2 | 2 | 6.6 | 6.582 | 0.018 |
| 3 | 1 | 6.592 | 6.569 | 0.023 |
| 4 | 1 | 6.62 | 6.599 | 0.021 |
| 5 | 2 | 6.612 | 6.595 | 0.017 |
| 6 | 1 | 6.608 | 6.59 | 0.018 |
| 7 | 1 | 6.616 | 6.597 | 0.019 |
| 8 | 2 | 6.615 | 6.597 | 0.018 |
| 9 | 1 | 6.617 | 6.599 | 0.018 |
| 10 | 2 | 6.602 | 6.584 | 0.018 |
| 11 | 2 | 6.615 | 6.597 | 0.018 |
| 12 | 1 | 6.616 | 6.597 | 0.019 |
| 13 | 2 | 6.602 | 6.584 | 0.018 |
| 14 | 1 | 6.608 | 6.589 | 0.019 |

TABLE 12

Individual Dose Accuracy of NARCAN ® Nasal Spray

| Subject | Period | Device Weight Before Dosing | Device Weight After Dosing | Device Weight Difference |
|---|---|---|---|---|
| 1 | 1 | 5.216 | 5.112 | 0.104 |
| 2 | 1 | 5.194 | 5.089 | 0.105 |
| 3 | 2 | 5.192 | 5.092 | 0.1 |
| 4 | 2 | 5.209 | 5.106 | 0.103 |
| 5 | 1 | 5.199 | 5.093 | 0.106 |
| 6 | 2 | 5.19 | 5.085 | 0.105 |
| 7 | 2 | 5.192 | 5.086 | 0.106 |
| 8 | 1 | 5.181 | 5.07 | 0.111 |
| 9 | 2 | 5.208 | 5.107 | 0.101 |
| 10 | 1 | 5.188 | 5.084 | 0.104 |
| 11 | 1 | 5.197 | 5.097 | 0.1 |
| 12 | 2 | 5.189 | 5.081 | 0.108 |
| 13 | 1 | 5.173 | 5.068 | 0.105 |
| 14 | 2 | 5.211 | 5.11 | 0.101 |

Conclusion

Study NP-001 was designed based on the FDA draft guidance Naloxone Hydrochloride (2017) and the Summary Review of Regulatory Action (2015) for NARCAN® Nasal Spray where it was determined that designing an efficacy study to define an effective range of naloxone used in the proposed setting would be difficult to justify as it would require administration of opioids to create an overdose, albeit in a controlled setting. Therefore, given the known safety profile of naloxone, the approach required by the division was to conduct a relative bioavailability study in healthy subjects that demonstrated the new product matched or exceeded the PK parameters of $C_{max}$ and $T_{max}$ for naloxone by an approved route. It was noted that the first few minutes were of particular importance, because if the overdose has led to apnea, time is of the essence if the brain is to be spared permanent hypoxic injury. Therefore, in addition to $C_{max}$ and $T_{max}$, it was necessary to demonstrate that the naloxone levels were comparable to the approved route during the first minutes after dosing.

The dose accuracy data from Study NP-001 supports that patients received comparable doses of both FMXIN001 Microspheres Nasal Powder and NARCAN® Nasal Spray demonstrated that FMXIN001 Microspheres Nasal Powder 4 mg displayed greater peak and total systemic exposure, with earlier onset of action (supported by greater partial exposures) for total and unconjugated naloxone when compared to NARCAN® Nasal Spray 4 mg after a single dose in healthy subjects under fasted conditions, supporting the potential benefit of overdose subjects to absorb naloxone more quickly in those first few critical minutes. Further, no SAEs were reported and no TEAEs led to discontinuation by any subject. FMXIN001 Microspheres Nasal Powder demonstrated a similar safety profile to NARCAN® Nasal Spray 4 mg.

Example 34: Nasal Cast Deposition Using Unitdose Device with a Microspheres Naloxone Powder Device: Unitdose powder device was provided by Aptar as described above. The Caucasian male nasal cast (was developed by Aptar in collaboration with Nasus Pharma). Naloxone HCl microspheres blend with lactose was prepared at Formulex for Nasus Pharma, Noramco API was used.

The deposition of the Naloxone in the Nasal Cast was studied by application of the Unitdose device loaded with 20 mg of Naloxone hydrochloride powder formulation. The assay of Naloxone HCl was 20.6%, i.e. about 4.1 mg of drug was applied by actuation.

Tests were performed in Aptar laboratory on a Caucasian male nasal cast using a specific "Jig" which assures specific:
Holding angle: 450
Angle from central wall: 4°
Insertion depth: 15 mm Three trials were performed. Two doses were delivered each time, one dose in each nostril. Samples were collected from the nasal cast by rinsing each region of interest with water. The content of Naloxone was analyzed spectrophotometrically at 229 nm.

Study Results:
The mass of naloxone recovered in all regions of interest are summarized in Table 13.

TABLE 10

Mass of Naloxone recovered in each region of interest

| Naloxone (in µg) | Trial 1 | Trial 2 | Trial 3 |
|---|---|---|---|
| Nose and Nasal valve | 573 | 318 | 443 |
| Floor | 125 | 256 | 119 |
| Turbinates (Middle) | 2917 | 2172 | 3165 |
| Olfactory Area | 3830 | 4048 | 4129 |
| Rhino-Pharynx | 383 | 477 | 433 |
| Filter/Lungs | 47 | 59 | 29 |
| Total recovery | 7876 | 7328 | 8317 |
| Overall Mean | | 7840 | |
| Overall SD | | 495 | |

The expected value of naloxone upon 2 doses administration is 8200 µg. The high and reproducible recovery of 95.6% evidences high experiments quality.

Figure 22:
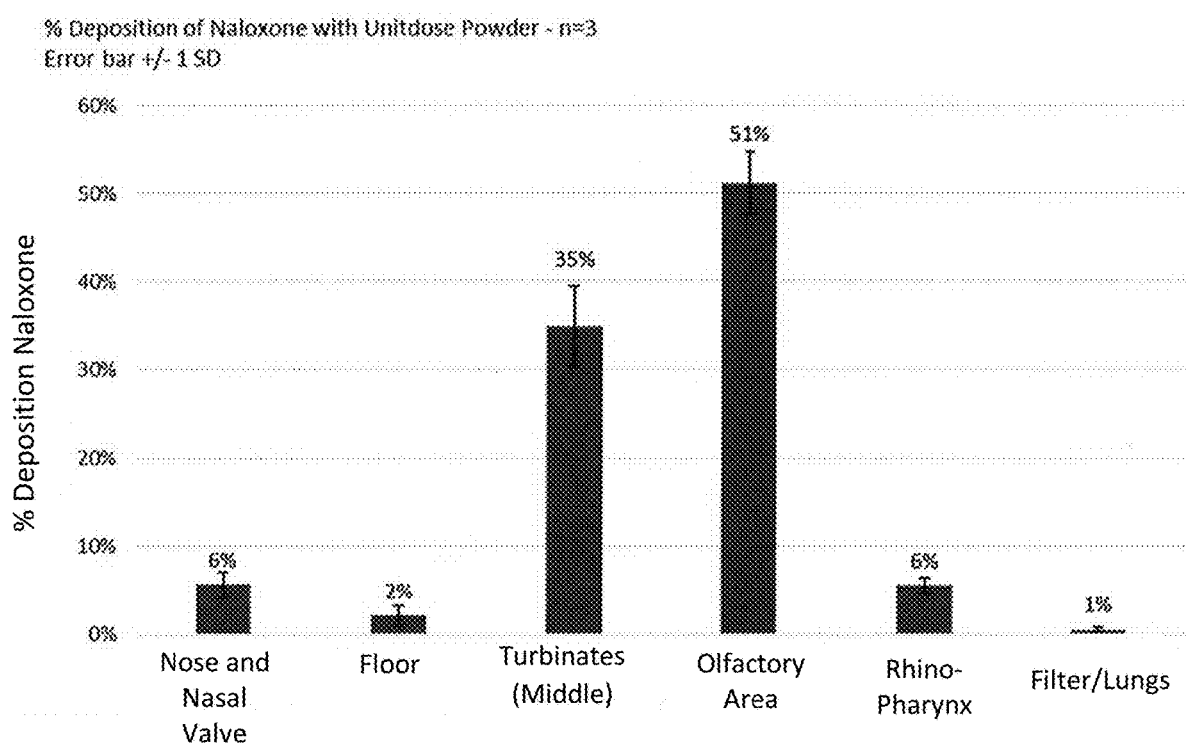
FIG. 22 shows the percentage deposition of Naloxone in each region of interest in the Nasal Cast (Example 34)

Table 14 and FIG. 22 summarize the percentage deposition of naloxone in each region of interest.

TABLE 11

% Naloxone in each Region of Interest

| Naloxone (in μg) | Trial 1 | Trial 2 | Trial 3 | Overall mean | Overall SD |
|---|---|---|---|---|---|
| Nose and Nasal valve | 7 | 4 | 5 | 6 | 1 |
| Floor | 2 | 3 | 1 | 2 | 1 |
| Turbinates (Middle) | 37 | 30 | 38 | 35 | 5 |
| Olfactory Area | 49 | 55 | 50 | 51 | 4 |
| Rhino-Pharynx | 5 | 7 | 5 | 6 | 1 |
| Filter/Lungs | 1 | 1 | 0 | 1 | 0 |

As shown, when the naloxone intranasal powder composition in accordance with the present disclosure was administered by means of a unitdose device for intranasal administration loaded with the composition, a high proportion of the naloxone particle of at least 86% reached the turbinates region, more specifically about 35% were the middle part and 51% in the upper olfactory area. Less than 10% of the naloxone particles were in the nose and less than 1% reached the lungs.

LIST OF REFERENCES

1. Alok Pratap Singh, Shailendra K. Saraf, Shubhini A. Saraf. SLN approach for nose-to-brain delivery of alprazolam, Drug delivery and Translational Research, 2012, vol. 2, Issue 6, pp 498-507
2. Kosfeld M, Heinrichs M, Zak P J, Fishbacher U, Fehr E: OxyContin increases trust in humans. Nature, 2005, vol. 435, pp 637-676
3. Benedict C, Hallshmid M, Schultes B, Born J, Kern W; Intranasal insulin to improve memory function in humans. Neuroendocrinology, 2007, vol. 86, pp 136-142
4. Freiherr J et al., Intranasal Insulin as a Treatment for Alzheimer's Disease: A Review of Basic Research and Clinical Evidence, CNS Drugs 2013, vol. 27, pp 505-514
5. Reger M A, Watson G S, Frey W H $2^{nd}$ et al., Effect of intranasal insulin on cognition in memory impaired older adults: modulation by APOE genotype. Neurobiol. Aging, 2006, vol. 27, pp 451-458
6. Kunlin Jin MD, David A. Greenberg et al, Cerebral neurogenesis is induced by intranasal administration of growth factors; Ann. Neurol. 2003, vol. 53, pp 405-409
7. Jennifer L. Sherr et al, Glucagon Nasal Powder: A Promising Alternative to Intramuscular Glucagon in Youth with Type 1 Diabetes, Diabetes Care 2016; vol. 39, pp 555-562.
8. EMA Guideline: Guideline on the Pharmaceutical Quality of Inhalation and Nasal Products (June 2006); FDA Guidance for Industry (Chemistry, Manufacturing & Controls Documentation): Metered-Dose Inhaler (MDI) & Dry Powder Inhaler (DPI) Drug Products (October 1998).
9. Nasal Spray and Inhalation Solution, Suspension, and Spray Drug Products—Chemistry, Manufacturing, and Controls Documentation, July 2002.
10. Mohammad Obaidi et al., Improved Pharmacokinetics of Sumatriptan with Breath Powered™ Nasal Delivery of Sumatriptan Powder, Headache, 2013, vol. 53, pp 1323-1333
11. Fuseau E et al., Clinical pharmacokinetics of intranasal sumatriptan, Clin Pharmacokinet., 2002, vol. 41(11), pp 801-811.
12. United Nations Office on Drugs and Crime (UNODC). World Drug Report. 2016. United Nations publication, Sales No. E.16.XI.7. Available at: https://www.unodc.org/wdr2016/
13. Rudd R A, Aleshire N, Zibbell J E, Gladden R M. Increases in drug and opioid overdose deaths-United States, 2000-2014. Morbidity and Mortality Weekly Report (MMWR). 2016; 64(50-51):1378-1382.
14. Clarke S F, Dargan P I, Jones A L. Naloxone in opioid poisoning: walking the tightrope. Emerg Med J. 2005; 22(9):612-616.
15. Buajordet I, Naess A C, Jacobsen D, Brors O. Adverse events after naloxone treatment of episodes of suspected acute opioid overdose. Eur J Emerg Med. 2004; 11(1): 19-23.
16. Lewis C R, Vo H T, Fishman M. Intranasal naloxone and related strategies for opioid overdose intervention by nonmedical personnel: a review. Subs Abuse Rehab. 2017; 8:79-95
17. World Health Organization (2014) Community management of opioid overdose, WHO Guidelines Approved by the Guidelines Review Committee. World Health Organization, Geneva. Available at: http://apps.who.int/iris/bitstream/10665/137462/1/9789241548816 eng.pdf?ua=1&ua=1
18. NARCAN® (naloxone hydrochloride) Nasal Spray Prescribing Information. Adapt Pharma, Inc., USA. November 2015.
19. Food and Drug Administration (FDA). FDA moves quickly to approve easy-to-use nasal spray to treat opioid overdose, 2015. Available at: http://www.fda.gov/NewsEvents/Newsroom/PressAnnouncements/ucm473505.htm
20. Nyxoid-Epar-Product-Information. Mundipharma Corporation (Ireland) Ltd. November 2017
21. Clement J G, Copeman H T: Soman and sarin induce a long-lasting naloxone-reversible analgesia in mice. Life Sci. 1984, 34: 1415-1422

The invention claimed is:

1. A pharmaceutical composition in a form of dry powder for intranasal administration, comprising at least one opioid receptor antagonist as active ingredient, said composition comprising (1) at least one opioid receptor antagonist solid particles and (2) pharmaceutically acceptable disaggregating agent solid particles, wherein at least 90% of said one opioid receptor antagonist solid particles are of a mean particle size of about 10 to about 30 microns, and less than about 10% of said at least one opioid receptor antagonist solid particles are of a mean particle size equal to or below about 10 microns and said pharmaceutically acceptable disaggregating agent solid particles are of a mean particle size greater than that of said at least one opioid receptor antagonist solid particles.

2. The pharmaceutical composition according to claim 1, wherein less than about 5% of said at least one opioid receptor antagonist solid particles are of a mean particle size of or below 5 microns.

3. The pharmaceutical composition of claim 1, wherein said pharmaceutically acceptable disaggregating agent solid particles are of a mean size of about 50 to about 200 microns.

4. The pharmaceutical composition of claim 1, wherein said pharmaceutically acceptable disaggregating agent solid particles are of a mean size of about 50 to about 150 microns.

5. The pharmaceutical composition of claim 1, wherein said at least one opioid receptor antagonist solid particles are of a substantially spherical form and said pharmaceutically acceptable disaggregating agent solid particles are of an irregular shape.

6. The pharmaceutical composition of claim 1, comprising said disaggregating agent as the only excipient for preventing aggregation of the dry powder particles of the active ingredient and preserving their original size and shape in said composition.

7. The pharmaceutical composition of claim 1, wherein said at least one opioid receptor antagonist is any one of naloxone, naltrexone, almivopan, methylnaltrexone, naloxegon or naldemidine and pharmaceutically acceptable salts thereof and solvates or hydrates thereof, wherein said salt is any of chloride, bromide, oxalate, or tosylate.

8. The pharmaceutical composition of claim 1, wherein said disaggregating agent is any one of lactose monohydrate, lactose, a lactose functional analogue, dextrose, sorbitol, mannitol, maltitol and xylitol, a cellulose or cellulose derivative, or starch or starch derivative, or any mixture of at least two thereof.

9. The pharmaceutical composition of claim 1, wherein the weight ratio between said at least one opioid receptor antagonist solid particles and said pharmaceutically acceptable disaggregating agent solid particle is between about 1:9 to about 9:1.

10. A disposable dose unit for single intranasal administration to a subject of a pharmaceutical composition according to claim 1, wherein said dose unit is loaded with a predetermined dose of the composition and provides the subject with a therapeutically effective metered dose of said opioid receptor antagonist.

11. A method of treating opioid overdose/intoxication and/or a symptom thereof in a patient in need thereof, said method comprising intranasally administering to said patient a therapeutically effective amount of a composition as defined in claim 1.

12. The method of claim 11, wherein said symptom associated with opioid overdose/intoxication is any one of respiratory depression, central nervous system depression, cardiovascular depression, altered level consciousness, miotic pupils, hypoxemia, acute lung injury, aspiration pneumonia, sedation, hypotension, unresponsiveness to stimulus, unconsciousness, stopped breathing; erratic or stopped pulse, choking or gurgling sounds, blue or purple fingernails or lips, slack or limp muscle tone, contracted pupils, and vomiting.

13. The method of claim 11, further comprising administration of an opioid, wherein said opioid is administered simultaneously with said opioid receptor antagonist or separately.

14. The method of claim 11, wherein said intranasal administration results in over 50% of said at least one opioid receptor antagonist solid particles reaching turbinates region in the intranasal cavity, and less than 1% of said at least one opioid receptor antagonist solid particles reaching the lungs of said patient.

15. A naloxone pharmaceutical composition in the form of dry powder for intranasal administration, comprising as active agent naloxone or a pharmaceutically acceptable salt thereof, said composition comprising (1) naloxone or pharmaceutically acceptable salt thereof solid particles, and (2) lactose monohydrate solid particles as disaggregation agent, wherein at least about 90% of said naloxone or pharmaceutically acceptable salt thereof solid particles are of a mean particle size of about 10-30 microns and less than about 10% of said naloxone or pharmaceutically acceptable salt thereof solid particles are of a mean particle size equal to or below about 10 microns and said lactose monohydrate solid particles are of a mean particle size greater than that of said naloxone or pharmaceutically acceptable salt thereof solid particles, providing a metered therapeutically effective nominal dose of said naloxone or pharmaceutically acceptable salt thereof.

16. The naloxone pharmaceutical composition of claim 15, comprising 20% w/w, 15% w/w, 10% w/w, 8% w/w or 5% w/w naloxone or said pharmaceutically acceptable salt thereof or solvate or hydrate thereof.

17. The naloxone pharmaceutical composition of claim 15, wherein said therapeutically effective nominal dose of said naloxone is 4 mg.

18. A disposable dose unit for single intranasal administration to a subject of a naloxone pharmaceutical composition according to claim 15, wherein said dose unit is loaded with a predetermined dose of the composition and provides the subject with a therapeutically effective metered dose of naloxone or said pharmaceutically acceptable salt thereof.

19. The disposable dose unit of claim 18, wherein said therapeutically effective metered dose of naloxone or said pharmaceutically acceptable salt thereof is 4 mg per single administration.

20. A kit for intranasal administration of naloxone comprising:
   a. at least one dose unit for single intranasal administration comprising a naloxone pharmaceutical composition as defined in claim 15; and
   b. instructions for use.

21. A method of treating opioid overdose/intoxication and/or a symptom thereof in a patient in need thereof, said method comprising intranasally administering to said patient a therapeutically effective dose of a composition as defined in claim 15.

22. The method of claim 21, wherein administration of said therapeutically effective dose is repeated at 2 to 3 minute intervals, up to a cumulative dose of from about 8 mg to about 10 mg and up to about 15 mg of naloxone.

23. The method of claim 21, further comprising administration of an opioid, wherein said opioid is administered simultaneously with said naloxone or separately.

* * * * *